United States Patent
Samec et al.

(10) Patent No.: US 11,460,705 B2
(45) Date of Patent: *Oct. 4, 2022

(54) AUGMENTED REALITY SPECTROSCOPY

(71) Applicant: Magic Leap, Inc., Plantation, FL (US)

(72) Inventors: Nicole Elizabeth Samec, Ft. Lauderdale, FL (US); Nastasja U. Robaina, Coconut Grove, FL (US); Adrian Kaehler, Los Angeles, CA (US); Mark Baerenrodt, Millbrae, CA (US); Eric Baerenrodt, Milford, NH (US); Christopher M. Harrises, Nashua, NH (US); Tammy Sherri Powers, Coral Springs, FL (US)

(73) Assignee: Magic Leap, Inc., Plantation, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/391,889

(22) Filed: Aug. 2, 2021

(65) Prior Publication Data
US 2022/0026717 A1      Jan. 27, 2022

Related U.S. Application Data

(63) Continuation of application No. 16/775,123, filed on Jan. 28, 2020, now Pat. No. 11,079,598, which is a continuation of application No. 15/713,420, filed on Sep. 22, 2017, now Pat. No. 10,558,047.
(Continued)

(51) Int. Cl.
*G02B 27/01*     (2006.01)
*G01J 3/02*      (2006.01)
(Continued)

(52) U.S. Cl.
CPC ........ *G02B 27/0172* (2013.01); *A61B 5/0075* (2013.01); *A61B 5/1114* (2013.01);
(Continued)

(58) Field of Classification Search
CPC .............. G02B 27/0172; G02B 27/017; G02B 27/0093; G02B 2027/0125;
(Continued)

(56) References Cited

U.S. PATENT DOCUMENTS 5,377,674 A    1/1995   Kuestner
6,850,221 B1   2/2005   Tickle
(Continued)

FOREIGN PATENT DOCUMENTS

JP    2002-150803        5/2002
JP    2002-150803 A      5/2002
(Continued)

OTHER PUBLICATIONS

International Search Report and Written Opinion for PCT Application No. PCT/US2017/53067, dated Dec. 8, 2017.
(Continued)

*Primary Examiner* — Peter D McLoone
(74) *Attorney, Agent, or Firm* — Knobbe, Martens, Olson & Bear, LLP

(57) ABSTRACT

In some embodiments, a system comprises a head-mounted frame removably coupleable to the user's head; one or more light sources coupled to the head-mounted frame and configured to emit light with at least two different wavelengths toward a target object in an irradiation field of view of the light sources; one or more electromagnetic radiation detectors coupled to the head-mounted member and configured to receive light reflected after encountering the target object; and a controller operatively coupled to the one or more light sources and detectors and configured to determine and display an output indicating the identity or property of the target object as determined by the light properties measured by the detectors in relation to the light properties emitted by the light sources.

16 Claims, 12 Drawing Sheets

Related U.S. Application Data

(60) Provisional application No. 62/398,454, filed on Sep. 22, 2016.

(51) Int. Cl.

| | | |
|---|---|---|
| *G01J 3/42* | (2006.01) | |
| *A61B 5/1455* | (2006.01) | |
| *A61B 5/11* | (2006.01) | |
| *A61B 5/00* | (2006.01) | |
| *G06F 3/03* | (2006.01) | |
| *G01J 3/10* | (2006.01) | |
| *G06F 3/01* | (2006.01) | |
| *G01J 3/28* | (2006.01) | |
| *G01J 3/427* | (2006.01) | |
| *G01N 21/359* | (2014.01) | |
| *G01N 33/483* | (2006.01) | |
| *F21V 8/00* | (2006.01) | |
| *G02B 27/00* | (2006.01) | |

(52) U.S. Cl.
CPC ........ *A61B 5/1121* (2013.01); *A61B 5/14551* (2013.01); *A61B 5/6803* (2013.01); *A61B 5/743* (2013.01); *A61B 5/744* (2013.01); *G01J 3/0248* (2013.01); *G01J 3/0256* (2013.01); *G01J 3/0264* (2013.01); *G01J 3/10* (2013.01); *G01J 3/108* (2013.01); *G01J 3/2823* (2013.01); *G01J 3/42* (2013.01); *G01J 3/427* (2013.01); *G01N 21/359* (2013.01); *G01N 33/483* (2013.01); *G02B 6/0076* (2013.01); *G02B 27/017* (2013.01); *G06F 3/011* (2013.01); *G06F 3/013* (2013.01); *G06F 3/0304* (2013.01); *G01J 2003/106* (2013.01); *G01J 2003/2826* (2013.01); *G01J 2003/425* (2013.01); *G02B 27/0093* (2013.01); *G02B 2027/014* (2013.01); *G02B 2027/0125* (2013.01); *G02B 2027/0138* (2013.01); *G02B 2027/0187* (2013.01); *G06F 3/012* (2013.01)

(58) Field of Classification Search
CPC ...... G02B 2027/0138; G02B 2027/014; G02B 2027/0187; A61B 5/0075; A61B 5/1114; A61B 5/14551; A61B 5/6803; A61B 5/743; A61B 5/744; G01J 3/0248; G01J 3/0256; G01J 3/0264; G01J 3/10; G01J 3/108; G01J 3/2823; G01J 3/42; G01J 3/427; G01J 2003/106; G01J 2003/2826; G01J 2003/425; G01N 33/483; G06F 3/011; G06F 3/012; G06F 3/013; G06F 3/0304
See application file for complete search history.

(56) References Cited

U.S. PATENT DOCUMENTS

| | | | |
|---|---|---|---|
| 7,286,287 B1 | 10/2007 | Ofner | |
| 8,248,458 B2 | 8/2012 | Schowengerdt et al. | |
| 8,950,867 B2 | 2/2015 | Macnamara | |
| 9,044,163 B2 * | 6/2015 | Yamaguchi | A61B 1/000094 |
| 9,081,426 B2 | 7/2015 | Armstrong | |
| 9,215,293 B2 | 12/2015 | Miller | |
| 9,310,559 B2 | 4/2016 | Macnamara | |
| 9,348,143 B2 | 5/2016 | Gao et al. | |
| D758,367 S | 6/2016 | Natsume | |
| 9,417,452 B2 | 8/2016 | Schowengerdt | |
| 9,470,906 B2 | 10/2016 | Kaji et al. | |
| 9,547,174 B2 | 1/2017 | Gao et al. | |
| 9,671,566 B2 | 6/2017 | Abovitz et al. | |
| 9,740,006 B2 | 8/2017 | Gao | |
| 9,791,700 B2 | 10/2017 | Schowengerdt et al. | |
| 9,851,563 B2 | 12/2017 | Gao et al. | |
| 9,857,591 B2 | 1/2018 | Welch et al. | |
| 9,874,749 B2 | 1/2018 | Bradski | |
| 10,558,047 B2 | 2/2020 | Samec et al. | |
| 11,079,598 B2 | 8/2021 | Samec et al. | |
| 2001/0021108 A1 | 9/2001 | Shimada et al. | |
| 2002/0072658 A1 | 6/2002 | Rice et al. | |
| 2006/0028436 A1 | 2/2006 | Armstrong | |
| 2007/0031291 A1 | 2/2007 | Piech et al. | |
| 2007/0081123 A1 | 4/2007 | Lewis | |
| 2008/0117289 A1 | 5/2008 | Schowengerdt et al. | |
| 2010/0113940 A1 | 5/2010 | Sen et al. | |
| 2012/0127062 A1 | 5/2012 | Bar-Zeev et al. | |
| 2012/0154567 A1 | 6/2012 | Yamaguchi | |
| 2012/0162549 A1 | 6/2012 | Gao et al. | |
| 2013/0009993 A1 | 1/2013 | Horseman | |
| 2013/0082922 A1 | 4/2013 | Miller | |
| 2013/0117377 A1 | 5/2013 | Miller | |
| 2013/0125027 A1 | 5/2013 | Abovitz | |
| 2013/0208234 A1 | 8/2013 | Lewis | |
| 2013/0242262 A1 | 9/2013 | Lewis | |
| 2014/0039309 A1 | 2/2014 | Harris et al. | |
| 2014/0046291 A1 | 2/2014 | Harris et al. | |
| 2014/0071539 A1 | 3/2014 | Gao | |
| 2014/0160432 A1 | 6/2014 | Brown et al. | |
| 2014/0177023 A1 | 6/2014 | Gao et al. | |
| 2014/0213865 A1 | 7/2014 | Kobayashi et al. | |
| 2014/0218468 A1 | 8/2014 | Gao et al. | |
| 2014/0267420 A1 | 9/2014 | Schowengerdt | |
| 2014/0306866 A1 | 10/2014 | Miller et al. | |
| 2015/0016777 A1 | 1/2015 | Abovitz et al. | |
| 2015/0103306 A1 | 4/2015 | Kaji et al. | |
| 2015/0178939 A1 | 6/2015 | Bradski et al. | |
| 2015/0205126 A1 | 7/2015 | Schowengerdt | |
| 2015/0222883 A1 | 8/2015 | Welch | |
| 2015/0222884 A1 | 8/2015 | Cheng | |
| 2015/0250411 A1 | 9/2015 | Ma et al. | |
| 2015/0257735 A1 | 9/2015 | Ball et al. | |
| 2015/0268415 A1 | 9/2015 | Schowengerdt et al. | |
| 2015/0302652 A1 | 10/2015 | Miller et al. | |
| 2015/0309263 A2 | 10/2015 | Abovitz et al. | |
| 2015/0326570 A1 | 11/2015 | Publicover et al. | |
| 2015/0346490 A1 | 12/2015 | TeKolste et al. | |
| 2015/0346495 A1 | 12/2015 | Welch et al. | |
| 2016/0011419 A1 | 1/2016 | Gao | |
| 2016/0026253 A1 | 1/2016 | Bradski et al. | |
| 2016/0116739 A1 | 4/2016 | TeKolste et al. | |
| 2016/0249811 A1 | 9/2016 | Khan et al. | |
| 2016/0287153 A1 | 10/2016 | Samec et al. | |
| 2017/0205903 A1 | 7/2017 | Miller et al. | |
| 2020/0166760 A1 | 5/2020 | Samec | |

FOREIGN PATENT DOCUMENTS

| | | |
|---|---|---|
| JP | 2003-515759 | 5/2003 |
| JP | 2003-515759 A | 5/2003 |
| JP | 2006-139124 A | 6/2006 |
| JP | 2008-509438 A | 3/2008 |
| JP | 2009-505067 | 2/2009 |
| JP | 2012-125501 A | 7/2012 |
| JP | 5377674 | 12/2013 |
| JP | 2014-147473 | 8/2014 |
| KR | 2015-0136601 A | 12/2015 |
| KR | 2016-0008150 A | 1/2016 |
| KR | 2016-0091402 | 8/2016 |
| WO | WO 2006/017771 | 2/2006 |
| WO | WO 2014/015378 | 1/2014 |
| WO | WO 2015/094191 | 6/2015 |
| WO | WO 2015/175681 | 11/2015 |
| WO | WO 2016/123145 | 8/2016 |
| WO | WO 2016/127173 | 8/2016 |
| WO | WO 2018/057962 | 3/2018 |

OTHER PUBLICATIONS

International Preliminary Report for Patentability for PCT Application No. PCT/US2017/53067, dated Mar. 26, 2019.

(56) References Cited

OTHER PUBLICATIONS

ARToolKit: https://web.archive.org/web/20051013062315/http://www.hiti.washington.edu:80/artoolkit/documentation/hardware.htm, archived Oct. 13, 2005.

Azuma, "A Survey of Augmented Reality," Teleoperators and Virtual Environments 6, 4 (Aug. 1997), pp. 355-385. https://web.archive.org/web/20010604100006/http://www.cs.unc.edu/-azuma/ARpresence.pdf.

Azuma, "Predictive Tracking for Augmented Realty," TR95-007, Department of Computer Science, UNC-Chapel Hill, NC, Feb. 1995.

Bimber, et al., "Spatial Augmented Reality—Merging Real and Virtual Worlds," 2005 https://web.media.mit.edu/~raskar/book/BimberRaskarAugmentedRealityBook.pdf.

Jacob, "Eye Tracking in Advanced Interface Design," Human-Computer Interaction Lab Naval Research Laboratory, Washington, D.C. / paper/ in Virtual Environments and Advanced Interface Design, ed. By W. Barfield and T.A. Furness, pp. 258-288. Oxford University Press, New York (1995).

Tanriverdi and Jacob, "Interacting With Eye Movements in Virtual Environments," Department of Electrical Engineering and Computer Science, Tufts University, Medford, MA—paper/Proc. ACM CHI 2000 Human Factors in Computing Systems Conference, pp. 265-272, Addison-Wesley/ACM Press (2000).

\* cited by examiner

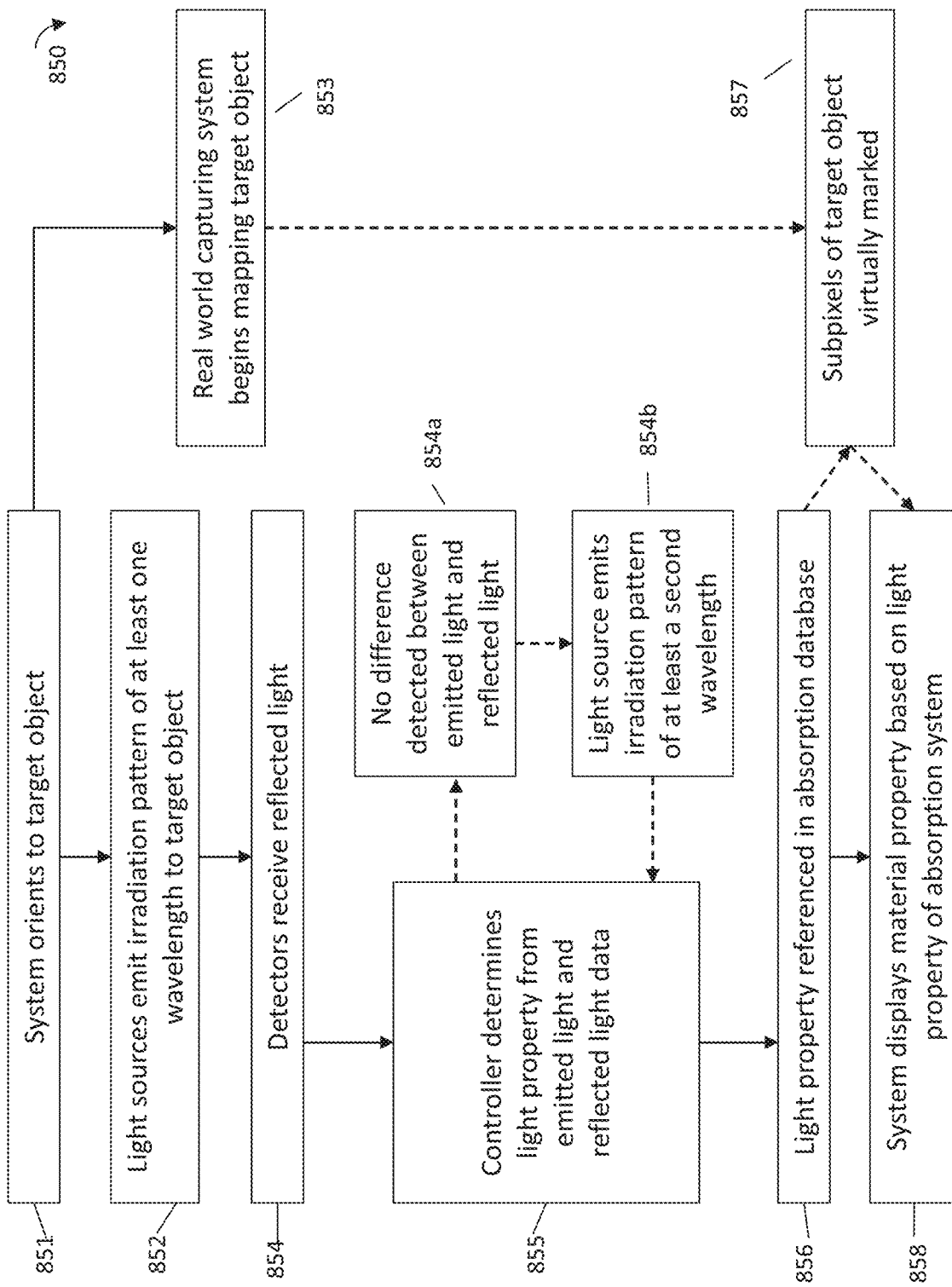

AUGMENTED REALITY SPECTROSCOPY

PRIORITY CLAIM

This application is a continuation of U.S. application Ser. No. 16/775,123, filed on Jan. 28, 2020, which is a continuation of U.S. application Ser. No. 15/713,420, filed on Sep. 22, 2017, which claims the benefit of priority of U.S. Provisional Application No. 62/398,454, filed on Sep. 22, 2016, all of which are incorporated herein by reference.

INCORPORATION BY REFERENCE

This application incorporates by reference the entireties of each of the following US patent applications: U.S. patent application Ser. No. 15/072,341; U.S. patent application Ser. No. 14/690,401; U.S. patent application Ser. No. 14/555,858; U.S. application Ser. No. 14/555,585; U.S. patent application Ser. No. 13/663,466; U.S. patent application Ser. No. 13/684,489; U.S. patent application Ser. No. 14/205,126; U.S. patent application Ser. No. 14/641,376; U.S. patent application Ser. No. 14/212,961; U.S. Provisional Patent Application No. 62/298,993 (corresponding to U.S. patent application Ser. No. 15/425,837); and U.S. patent application Ser. No. 15/425,837.

BACKGROUND

Field of the Invention

The present disclosure relates to systems and methods for augmented reality using wearable componentry, and more specifically to configurations of augmented reality systems for identifying material by reflective light properties.

Description of the Related Art

Modern computing and display technologies have facilitated the development of systems for so called "virtual reality" or "augmented reality" experiences, wherein digitally reproduced images or portions thereof are presented to a user in a manner wherein they seem to be, or may be perceived as, real. A virtual reality, or "VR", scenario typically involves presentation of digital or virtual image information without transparency to other actual real-world visual input; and an augmented reality or "AR" scenario typically involves presentation of digital or virtual image information as an augmentation to visualization of the actual world around the user while still permitting the user to substantially perceive and view the real world.

For example, referring to FIG. 1, an augmented reality scene (4) is depicted wherein a user of an AR technology sees a real-world park-like setting (6) featuring people, trees, buildings in the background, and a concrete platform (1120). In addition to these items, the user of the AR technology also perceives that he "sees" a robot statue (1110) standing upon the real-world platform (1120), and a cartoon-like avatar character (2) flying by which seems to be a personification of a bumble bee, even though these elements (2, 1110) do not exist in the real world. As it turns out, the human visual perception system is very complex, and producing a VR or AR technology that facilitates a comfortable, natural-feeling, rich presentation of virtual image elements amongst other virtual or real-world imagery elements is challenging. For instance, head-worn AR displays (or helmet-mounted displays, or smart glasses) typically are at least loosely coupled to a user's head, and thus move when the user's head moves. If the user's head motions are detected by the display system, the data being displayed can be updated to take the change in head pose into account. Certain aspects of suitable AR systems are disclosed, for example, in U.S. patent application Ser. No. 14/205,126, entitled "System and method for augmented and virtual reality," which is incorporated by reference in its entirety herein, along with the following additional disclosures, which relate to augmented and virtual reality systems such as those developed by Magic Leap, Inc. of Fort Lauderdale, Fla.: U.S. patent application Ser. No. 14/641,376; U.S. patent application Ser. No. 14/555,585; U.S. patent application Ser. No. 14/212,961; U.S. patent application Ser. No. 14/690,401; U.S. patent application Ser. No. 13/663,466; U.S. patent application Ser. No. 13/684,489; and U.S. Patent Application Ser. No. 62/298,993, each of which is incorporated by reference herein in its entirety.

Systems and methods disclosed herein address various challenges and developments related to AR and VR technology.

SUMMARY

A mixed reality system is configured to perform spectroscopy. Mixed reality (alternatively abbreviated as "MW") typically involves virtual objects integrated into and responsive to the natural world. For example, in an MR scenario, AR content by be occluded by real world objects and/or be perceived as interacting with other objects (virtual or real) in the real world. Throughout this disclosure, reference to AR, VR or MR is not limiting on the invention and the techniques may be applied to any context.

Some embodiments are directed to a wearable system for identifying substances (such as tissue, cells within tissue, or properties within cells/tissue) as a function of light wavelength emitted from and subsequently received by/reflected to/detected at a head-mounted member removably coupleable to a user's head. Though this disclosure mainly references tissue, or tissue properties, as a subject for analysis according to various embodiments, the technologies and techniques and components are not limited to such. Some embodiments utilize one or more light sources, such as electromagnetic radiation emitters coupled to the head-mounted member, to emit light in one or more wavelengths in a user-selected direction. Such embodiments permit continuous, and even passive, measurements. For example, a user wearing a head mounted system could conduct a given activity, but inward facing sensors could detect properties of the eye without interfering with the activity.

For example, a user could wear a system configured to look inward to the user's eyes and identify or measure tissue properties of the eye, such as blood concentration in a blood vessel of the eye. In other examples of inward systems, fluids such as intraocular fluid may be analyzed and not simply tissue properties. In other examples, a system could comprise sensors that look outward towards the external world and identify or measure tissue or material properties other than the eye, such as an extremity of the user or object in the ambient environment apart from the user.

In outward looking systems, eye tracking cameras coupled to the head-mounted member can determine the directional gaze a user is looking, and a processor or controller may correlate that gaze with observation of a real world target object through images captured from a real-world capturing system (such as cameras or depth sensors) coupled to the head-mounted member. Light sources coupled to the head-mounted system emit light away from the user, such as infrared light for example from an electromagnetic radiation emitter, and in some embodiments emit light to create an irradiation pattern in a substantially same direction as a gaze direction determined by the eye tracking cameras, thereby emitting upon the target object.

In some embodiments, real world capturing systems capture an object. For example a depth sensor, such as a vertical cavity surface emitting laser, may determine the outline of an object through collecting time of flight signals impacting the object. The object, once identified at its contours by such real-world capturing system may be highlighted and available for labeling. In some embodiments, a camera system of a given field of view defines an area available for highlighting and labelling. For example, a camera correlating to a user's gaze may encompass a 5 degree field of view, 10 degree field of view, or suitable increments preferably up to a 30 degree central vision field of view that the light source will emit light substantially within.

In some embodiments, such a system further comprises one or more electromagnetic radiation detectors or photodetectors coupled to the head-mounted member configured to receive reflected light that was emitted from the light source and reflected from the target object; and a controller operatively coupled to the one or more electromagnetic radiation emitters and one or more electromagnetic radiation detectors configured to cause the one or more electromagnetic radiation emitters to emit pulses of light while also causing the one or more electromagnetic radiation detectors to detect levels of light absorption related to the emitted pulses of light as a function of any received reflected light of a particular pulse emission.

In some embodiments, the system further comprises a processor to match a wavelength of reflected light received by a detector from the target object to a particular material, tissue type or property of an underlying tissue. In some embodiments other light characteristics are determined, such as polarization changes relative to emitted light and detected light or scattering effects, though for purposes of this description wavelength characteristics are used as an exemplary light characteristic. For example, in some embodiments, an inward electromagnetic radiation emitter emits light in the infrared spectrum to the retina of a user, receives reflected light, and matches the wavelength of the reflected light to determine a physical property such as the type of tissue or oxygen saturation in the tissue. In some embodiments, the system comprises outward facing light sources, and emits infrared light to a target object (such as an extremity of a user or third person), receives reflected light, and matches the reflected light wavelength to determine the observed material. For example, such an outward facing system may detect the presence of cancerous cells among healthy cells. Because cancerous, or other abnormal cells, reflect and absorb light differently than healthy cells, a reflection of light at certain wavelengths can indicate the presence and amount of abnormality.

In some embodiments, the controller receives the captured target object from the real world capturing system, and applies a label to the target object indicative of the identified property. In some embodiments, the label is a textual label or prompt within a display of the head mounted-member. In some embodiments, the label is an audio prompt to a user. In some embodiments, the label is a virtual image of similar tissue, such as referenced in a medical book, superimposed near the target object for ready comparative analysis by the user.

In some embodiments, the head-mounted member may comprise an eyeglasses frame. The eyeglasses frame may be a binocular eyeglasses frame. The one or more radiation emitters may comprise a light source, such as a light emitting diode. The one or more radiation emitters may comprise a plurality of light sources configured to emit electromagnetic radiation at two or more different wavelengths. The plurality of light sources may be configured to emit electromagnetic radiation at a first wavelength of about 660 nanometers, and a second wavelength of about 940 nanometers. The one or more radiation emitters may be configured to emit electromagnetic radiation at the two different wavelengths sequentially. The one or more radiation emitters may be configured to emit electromagnetic radiation at the two predetermined wavelengths simultaneously. The one or more electromagnetic radiation detectors may comprise a device selected from the group consisting of: a photodiode, a photodetector, and a digital camera sensor. The one or more electromagnetic radiation detectors may be positioned and oriented to receive light reflected after encountering a target object. The one or more electromagnetic radiation detectors may be positioned and oriented to receive light reflected after encountering observed tissue or material; that is, the one or more electromagnetic radiation detectors are oriented substantially in the same direction as the one or more electromagnetic radiation emitters, whether inward facing towards a user's eye or outward facing towards a user's environment.

The controller may be further configured to cause the plurality of light sources to emit a cyclic pattern of first wavelength on, then second wavelength on, then both wavelengths off, such that the one or more electromagnetic radiation detectors detect the first and second wavelengths separately. The controller may be configured to cause the plurality of light emitting diodes to emit a cyclic pattern of first wavelength on, then second wavelength on, then both wavelengths off, in a cyclic pulsing pattern about thirty times per second.

In some embodiments, the controller may be configured to calculate a ratio of first wavelength light measurement to second wavelength light measurement. In some embodiments this ratio may be further converted to an oxygen saturation reading via a lookup table based at least in part upon the Beer-Lambert law. In some embodiments, the ratio is converted to a material identifier in external lookup tables, such as stored in an absorption database module on a head-mounted member or coupled to a head-mounted member on a local or remote processing module. For example, an absorption database module for absorption ratios or wavelength reflection of particular tissues may be stored in a "cloud" storage system accessible by health care providers and accessed through a remote processing module. In some embodiments, an absorption database module may store absorption properties (such as wavelength ratios or wavelength reflections) for certain foods and be permanently stored on a local processing module to the head-mounted member.

In this way, the controller may be configured to operate the one or more electromagnetic radiation emitters and one or more electromagnetic radiation detectors to function as a broad use head-mounted spectroscope. The controller may be operatively coupled to an optical element coupled to the head-mounted member and viewable by the user, such that the output of the controller indicating the wavelength properties indicative of a particular tissue property or material otherwise may be viewed by the user through the optical element. The one or more electromagnetic radiation detectors may comprise a digital image sensor comprising a plurality of pixels, wherein the controller is configured to automatically detect a subset of pixels which are receiving the light reflected after encountering, for example, tissue or cells within the tissue. In some embodiments, such subset of pixels are used to produce an output representative of the target object within the field of view of the digital image sensor. For example, the output may be a display label that is indicative of an absorption level of the tissue. In some embodiments, comparative values are displayed as an output. For example, an output may be a percentage saturation of oxygen of blood from a first analysis time and a percentage saturation of oxygen at a second analysis time with a rate of change noted between the two times. In these embodiments, ailments such as diabetic retinopathy may be detected by recognizing changes in measured properties over time.

In some embodiments, the controller may be configured to automatically detect the subset of pixels based at least in part upon reflected light luminance differences amongst signals associated with the pixels. The controller may be configured to automatically detect the subset of pixels based at least in part upon reflected light absorption differences amongst signals associated with the pixels. In such embodiments, such subsets may be isolated pixels and flagged for further analysis, such as additional irradiation or mapping, or a virtual image may be overlaid on such pixels to provide visual contrast to the isolated pixels displaying other properties to serve as a notice to a user of the different properties of the subpixels identified by the system.

In some embodiments, the system data collection is time multiplexed not only for pulsing and recording light pulses, but passively collected at multiple times a day. In some embodiments, a GPS or other similar mapping system is coupled to the system to correlate a user's location or time of day with certain physiological data collected. For example, a user may track physiological responses relative to certain locations or activities throughout a day.

These and many other features and advantages of the present invention will be appreciated when the following figures and description are further taken into account.

BRIEF DESCRIPTION OF THE DRAWINGS

FIG. 8 illustrates a method for identifying materials or material properties through a head-mounted spectroscopy system according to some embodiments.

DETAILED DESCRIPTION

Some AR and VR systems comprise a processing capability, such as a controller or microcontroller, and also a power supply to power the function of the various components, and by virtue of the fact that at least some of the components in a wearable computing system, such as an AR or VR system, are close to the body of the user operating them, there is an opportunity to utilize some of these system components to conduct certain physiologic monitoring relative to the user. For example, physiologic monitoring may be conducted by measuring light absorption.

Figure 4B:
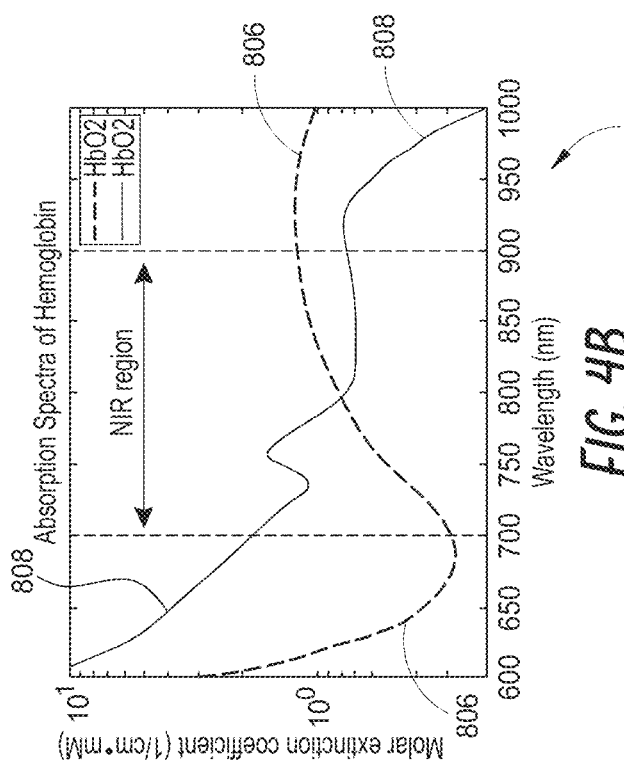
FIGS. 4A-4D illustrate various aspects of pulse oximetry configurations and calibration curves related to scattering of light in oxygenation of blood.
Figure 4A:
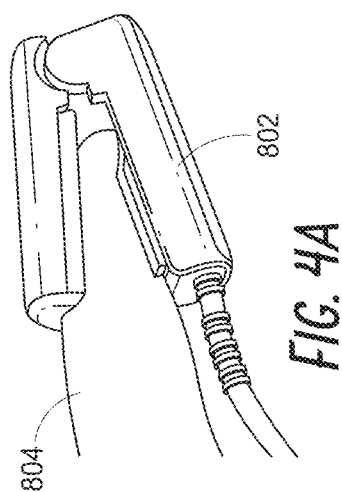

In conventional light absorption measurement techniques (for example pulse oximetry meters attachable to a person's finger as in FIG. 4A or in glucose detection), light is emitted in a controlled and fixed direction and received in a controlled and fixed receiver. Light is pulsed at different wavelengths through surrounding tissue structures while also being detected at another side of the tissue structure (and therefore measuring light properties such as absorption and scatter). In such systems, the measurement of light emitted compared to the measurement of light detected can provide an output that is proportional to, or reads as, an estimated tissue or tissue property (for example, an estimated blood oxygen saturation level for pulse oximetry meters), or simply a material or tissue type otherwise. Calibration curves depicting a ratio of light of interest relative to other light are also possible to predict properties of underlying tissue as a function of the light incident to it as shown in FIG. 4D.

Raman spectroscopy is another technique that measures inelastic scattering of photons released by irradiated molecules. Specific molecules will present specific shifts of wavelengths when irradiated, thereby presenting unique scattering effects that may be used to measure and quantify molecules within a sample.

FIG. 4B illustrates a chart of the absorption spectra of hemoglobin that is oxygenated (806) versus deoxygenated (808), and as shown in such plots (806, 808), in the red light wavelength range of the electromagnetic spectrum, such as around 660 nm, there is a notable difference in absorption for oxygenated versus deoxygenated hemoglobin, whereas there is an inverted difference at around 940 nm in the infrared wavelength range. Pulsing radiation at such wavelengths and detecting with a pulse oximeter is known to take advantage of such absorption differences in the determination of oxygen saturation for a particular user.

Figure 4C:
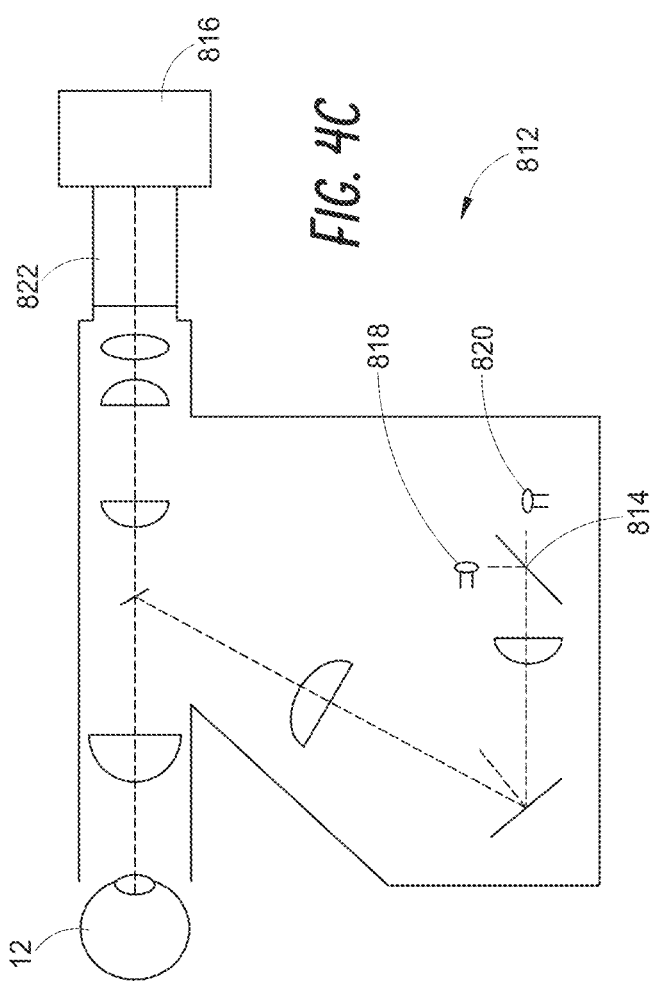
Figure 4D:
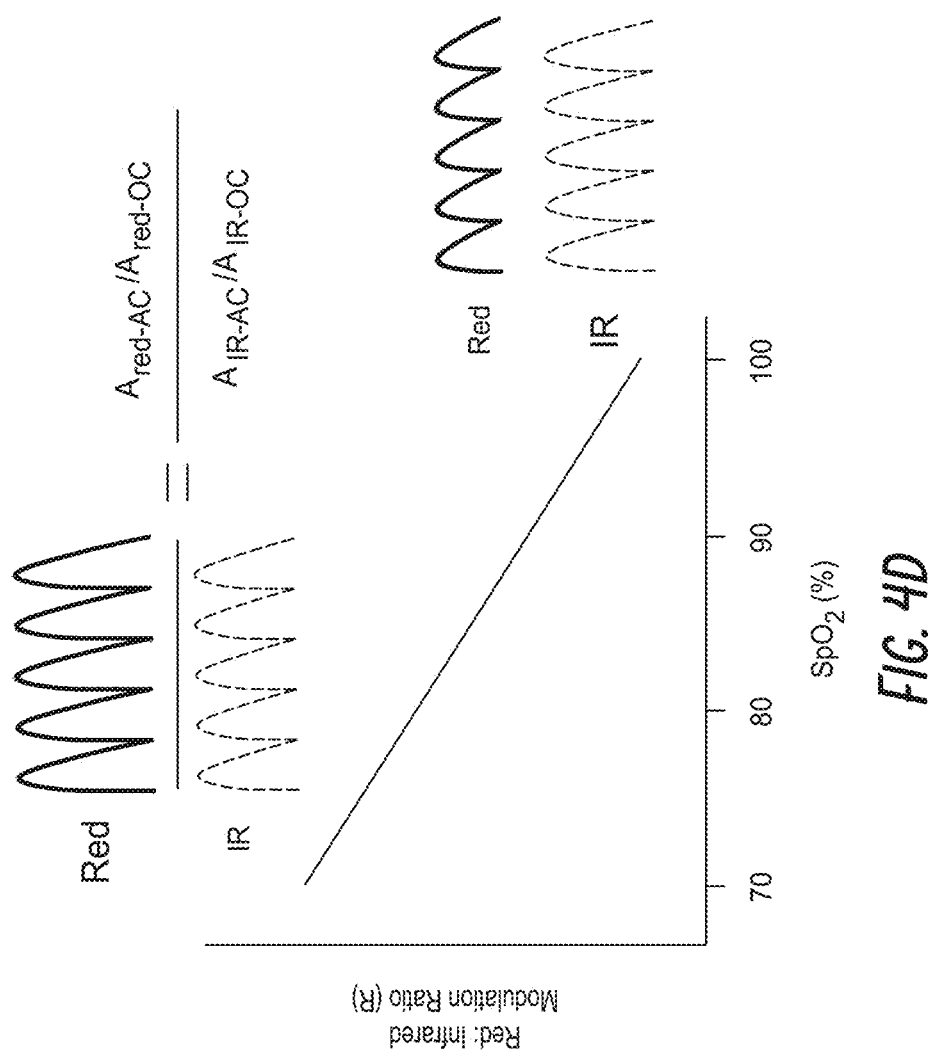

While pulse oximeters (802) typically are configured to at least partially encapsulate a tissue structure such as a finger (804) or ear lobe, certain desktop style systems have been suggested, such as that (812) depicted in FIG. 4C, to observe absorption differences in vessels of the eye, such as retinal vessels, but may be configured to detect properties of other tissues as well.

Such a configuration (812) may be termed a flow oximeter or spectroscope system and may comprise components as shown, including a camera (816), zoom lens (822), first (818) and second (820) light emitting diodes (LEDs), and one or more beam splitters (814). While it would be valuable to certain users, such as high-altitude hikers, athletes, or persons with certain cardiovascular or respiratory problems, to be able to retrieve information of their blood oxygen saturation as they move about their day and conduct their activities, or for caregivers to analyze tissue in real time for underlying abnormalities, most configurations involve a somewhat inconvenient encapsulation of a tissue structure, or are not portable or wearable, do not consider other absorption properties indicative of other tissue states or materials, or do not correlate gaze a user is looking at as part of directionality of its sensors (in other words, selectivity of target objects of for identification and analysis by spectroscopy is lacking).

Advantageously, in some embodiments, a solution is presented herein which combines the convenience of wearable computing in the form of an AR or VR system with an imaging means to determine additional tissue identification and properties in real time within a field of view of a user.

Referring to FIGS. 2A-2D, some general componentry options are illustrated. In the portions of the detailed description which follow the discussion of FIGS. 2A-2D, various systems, subsystems, and components are presented for addressing the objectives of providing a high-quality, comfortably-perceived display system for human VR and/or AR that access and create external information sources.

Figure 2A:
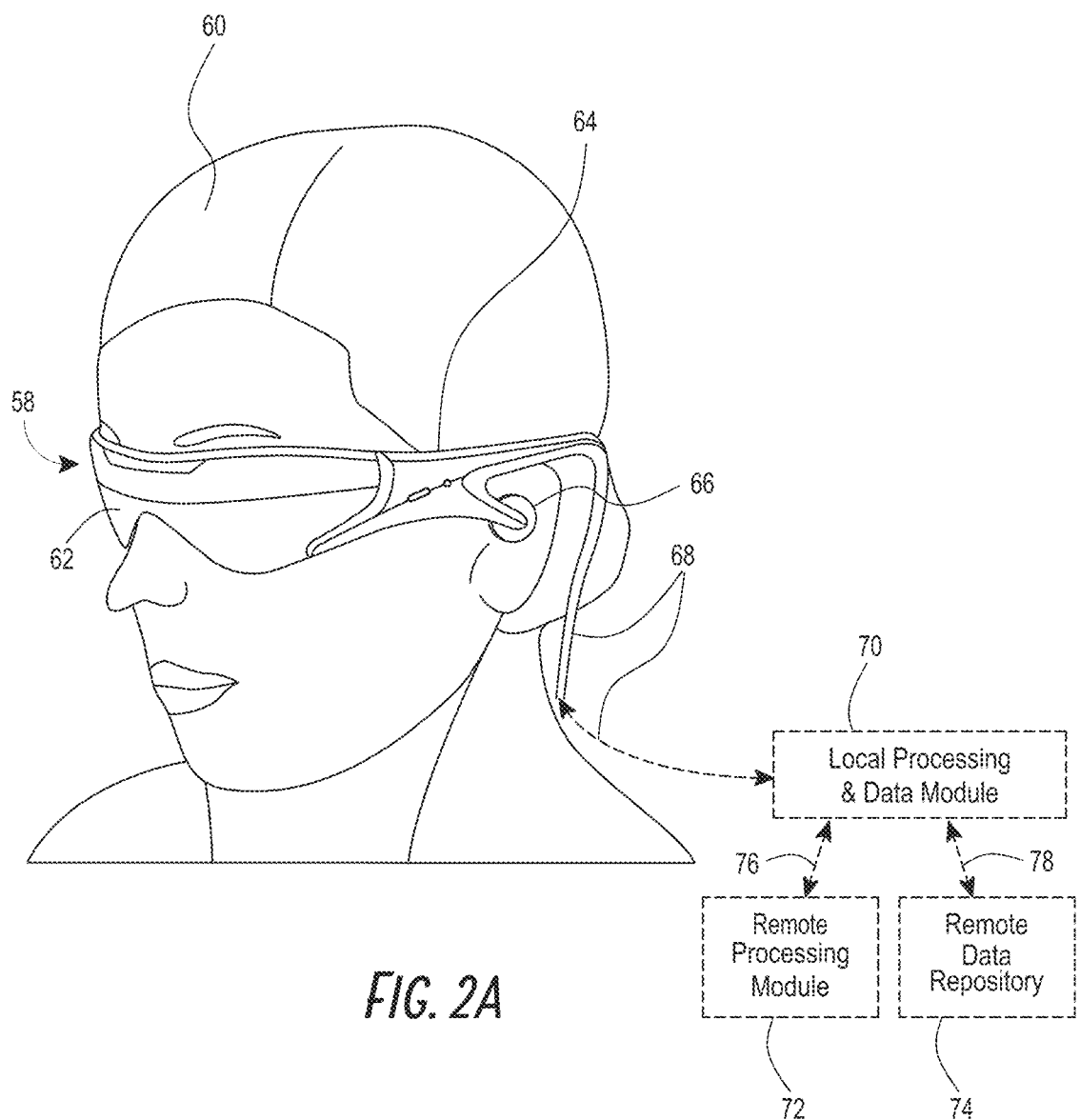
FIGS. 2A-2D illustrate certain aspects of various augmented reality systems for wearable computing applications, featuring a head-mounted component operatively coupled to local and remote process and data components.
Figure 2B:
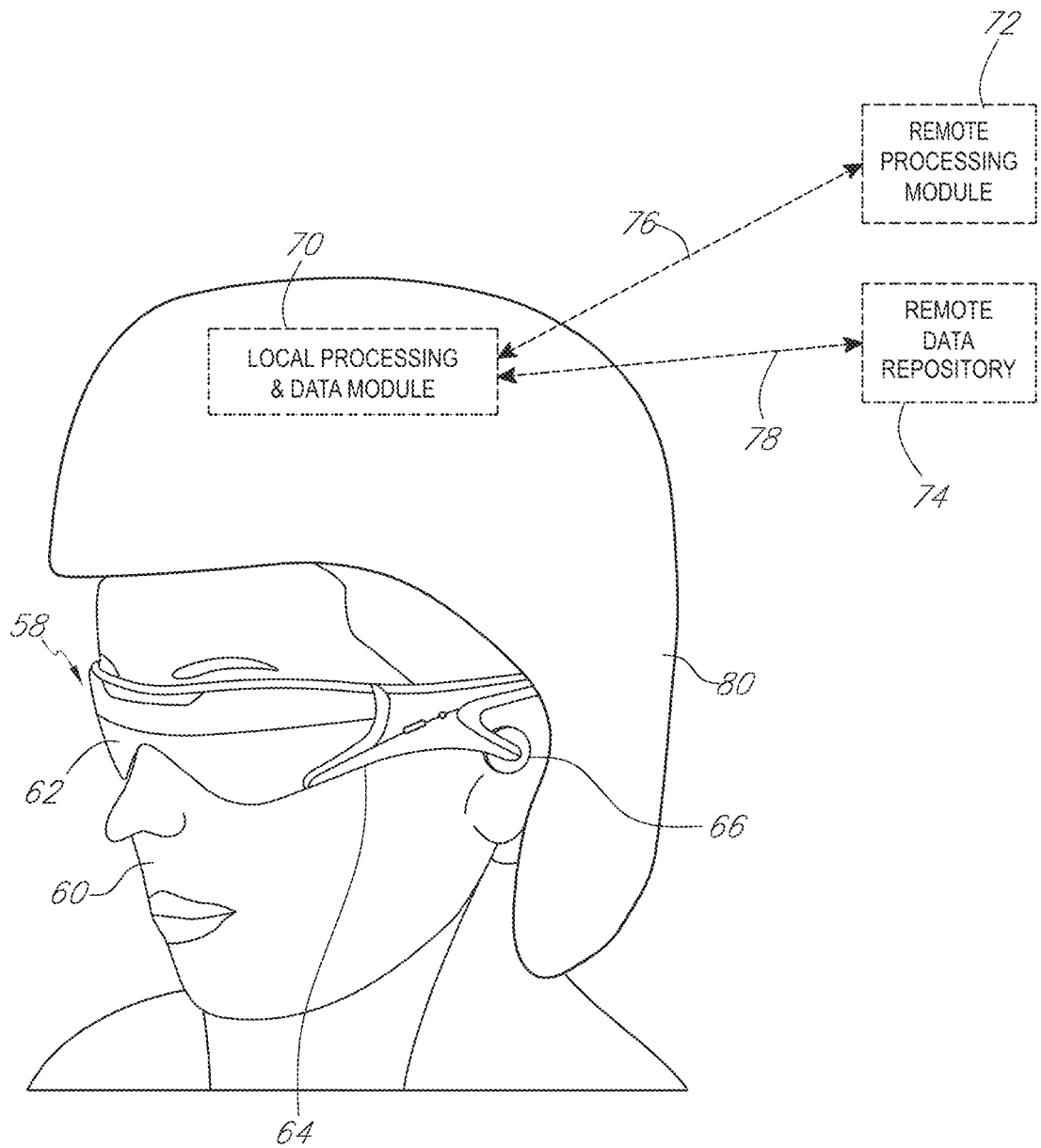
Figure 2C:
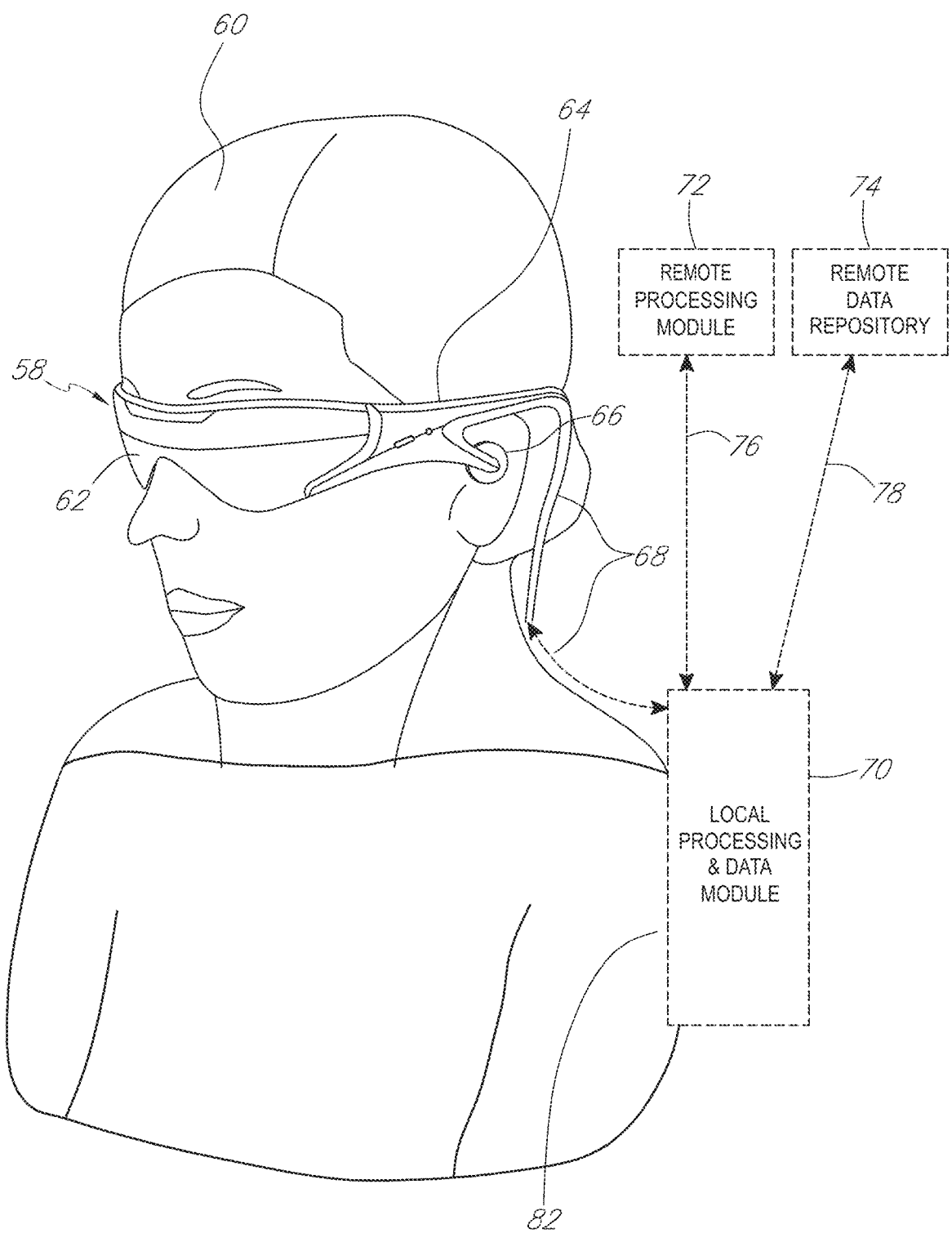
Figure 2D:
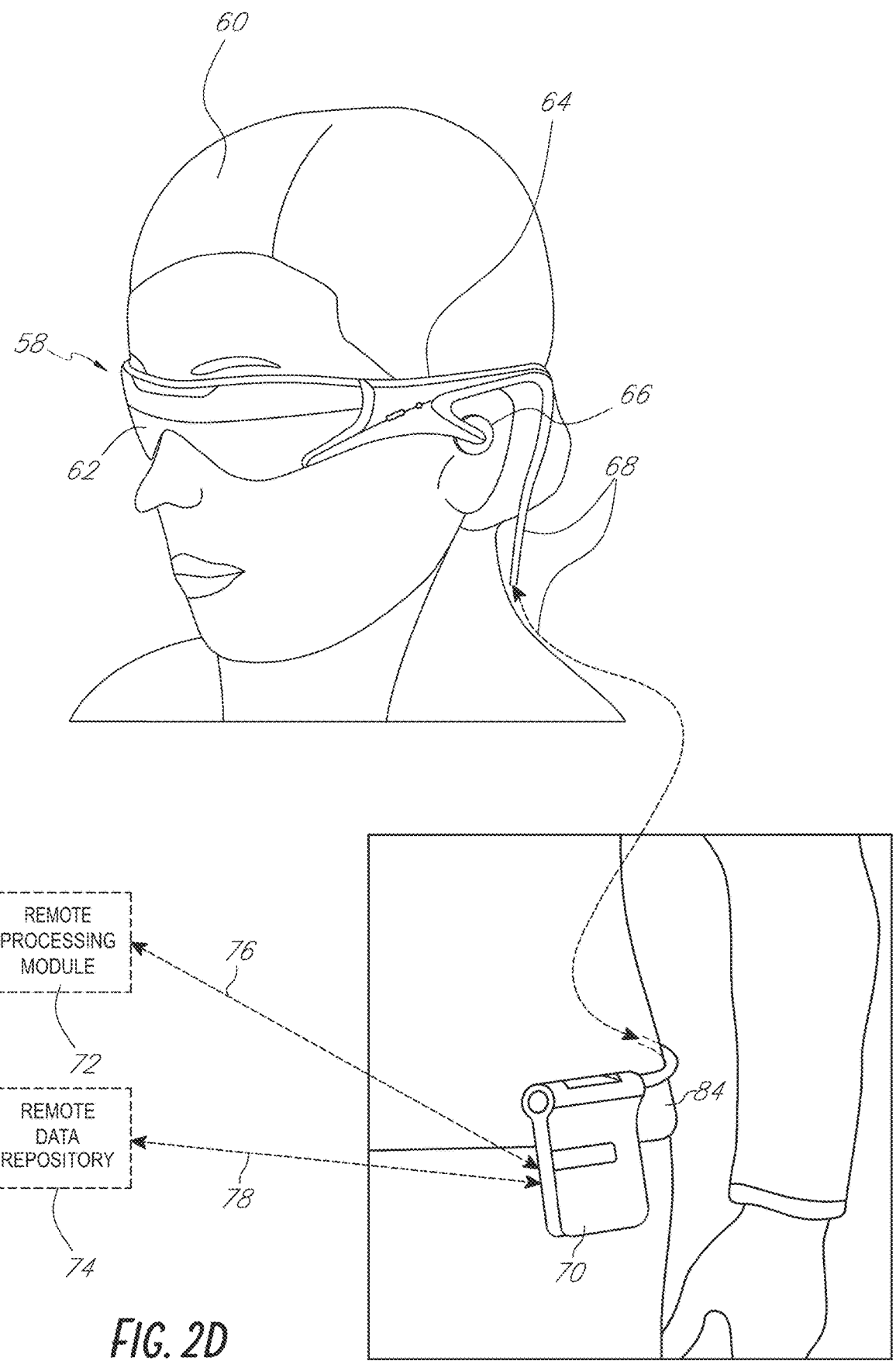

As shown in FIG. 2A, an AR system user (60) is depicted wearing head mounted component (58) featuring a frame (64) structure coupled to a display system (62) positioned in front of the eyes of the user. A speaker (66) is coupled to the frame (64) in the depicted configuration and positioned adjacent the ear canal of the user (in one embodiment, another speaker, not shown, is positioned adjacent the other ear canal of the user to provide for stereo/shapeable sound control). The display (62) is operatively coupled (68), such as by a wired lead or wireless connectivity, to a local processing and data module (70) which may be mounted in a variety of configurations, such as fixedly attached to the frame (64), fixedly attached to a helmet or hat (80) as shown in the embodiment of FIG. 2B, embedded in headphones, removably attached to the torso (82) of the user (60) in a backpack-style configuration as shown in the embodiment of FIG. 2C, or removably attached to the hip (84) of the user (60) in a belt-coupling style configuration as shown in the embodiment of FIG. 2D.

The local processing and data module (70) may comprise a processor or controller (e.g., a power-efficient processor or controller), as well as digital memory, such as flash memory, both of which may be utilized to assist in the processing, caching, and storage of data a) captured from sensors which may be operatively coupled to the frame (64), such as electromagnetic emitters and detectors, image capture devices (such as cameras), microphones, inertial measurement units, accelerometers, compasses, GPS units, radio devices, and/or gyros; and/or b) acquired and/or processed using the remote processing module (72) and/or remote data repository (74), possibly for passage to the display (62) after such processing or retrieval. The local processing and data module (70) may be operatively coupled (76, 78), such as via a wired or wireless communication links, to the remote processing module (72) and remote data repository (74) such that these remote modules (72, 74) are operatively coupled to each other and available as resources to the local processing and data module (70).

In one embodiment, the remote processing module (72) may comprise one or more relatively powerful processors or controllers configured to analyze and process data, light properties emitted or received, and/or image information. In one embodiment, the remote data repository (74) may comprise a relatively large-scale digital data storage facility, which may be available through the internet or other networking configuration in a "cloud" resource configuration. In one embodiment, all data is stored and all computation is performed in the local processing and data module, allowing fully autonomous use from any remote modules.

Figure 3:
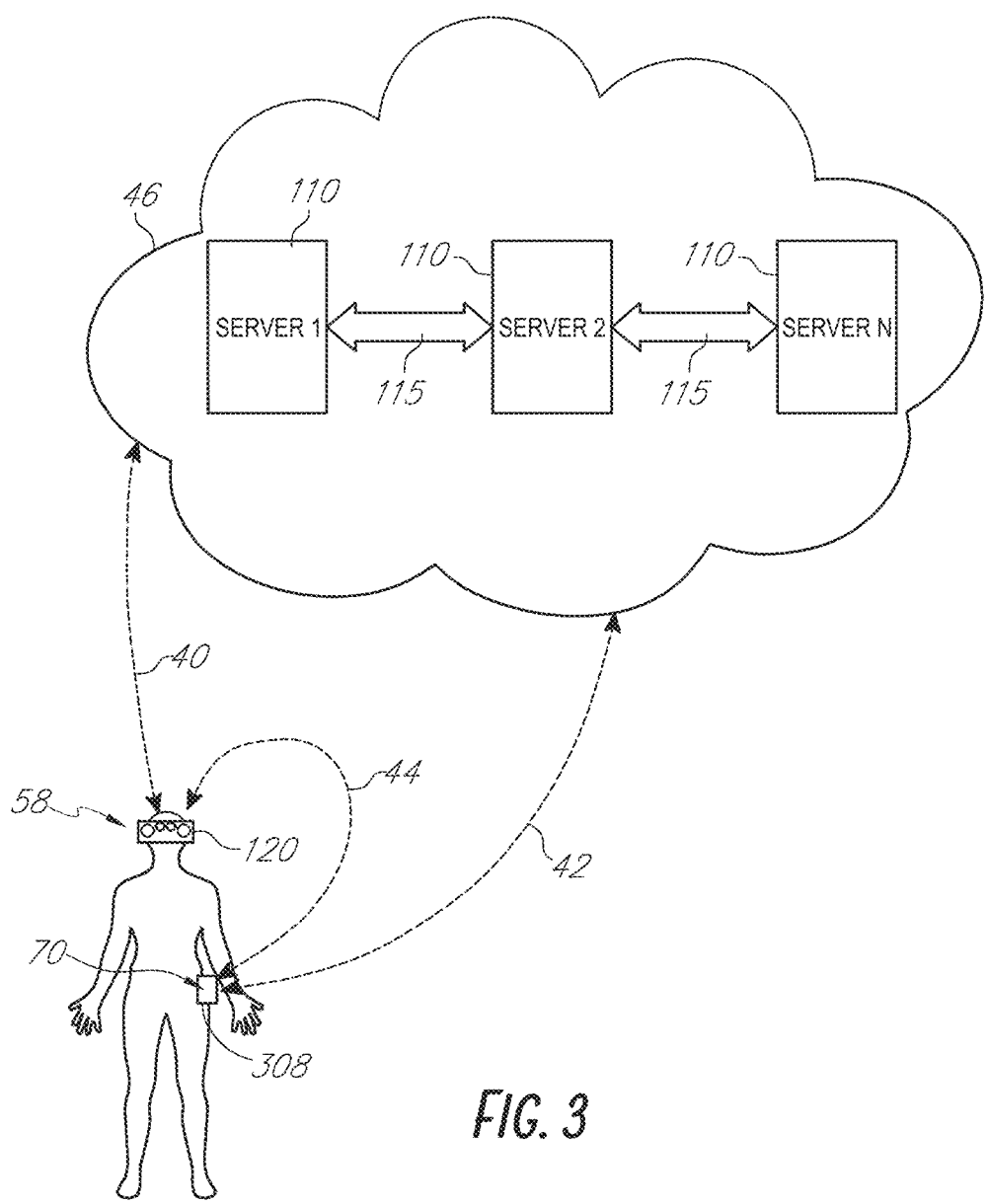
FIG. 3 illustrates certain aspects of a connectivity paradigm between a wearable augmented or virtual reality system and certain remote processing and/or data storage resources.

Referring now to FIG. 3, a schematic illustrates coordination between the cloud computing assets (46) and local processing assets, which may, for example reside in head mounted components (58) coupled to the user's head (120) and a local processing and data module (70), coupled to the user's belt (308); therefore the component 70 may also be termed a "belt pack" 70), as shown in FIG. 3. In one embodiment, the cloud (46) assets, such as one or more server systems (110) are operatively coupled (115), such as via wired or wireless networking (wireless generally being preferred for mobility, wired generally being preferred for certain high-bandwidth or high-data-volume transfers that may be desired), directly to (40, 42) one or both of the local computing assets, such as processor and memory configurations, coupled to the user's head (120) and belt (308) as described above. These computing assets local to the user may be operatively coupled to each other as well, via wired and/or wireless connectivity configurations (44), such as the wired coupling (68) discussed below in reference to FIG. 8.

In one embodiment, to maintain a low-inertia and small-size subsystem mounted to the user's head (120), primary transfer between the user and the cloud (46) may be via the link between the subsystem mounted at the belt (308) and the cloud, with the head mounted (120) subsystem primarily data-tethered to the belt-based (308) subsystem using wireless connectivity, such as ultra-wideband ("UWB") connectivity, as is currently employed, for example, in personal computing peripheral connectivity applications.

With efficient local and remote processing coordination, and an appropriate display device for a user, such as the user interface or user display system (62) shown in FIG. 2A, or variations thereof, aspects of one world pertinent to a user's current actual or virtual location may be transferred or "passed" to the user and updated in an efficient fashion. In other words, a map of the world may be continually updated at a storage location which may, e.g., partially reside on the user's AR system and partially reside in the cloud resources. The map (also referred to as a "passable world model") may be a large database comprising raster imagery, 3-D and 2-D points, parametric information and other information about the real world. As more and more AR users continually capture information about their real environment (e.g., through cameras, sensors, IMUs, etc.), the map becomes more and more accurate and complete.

Figure 1:
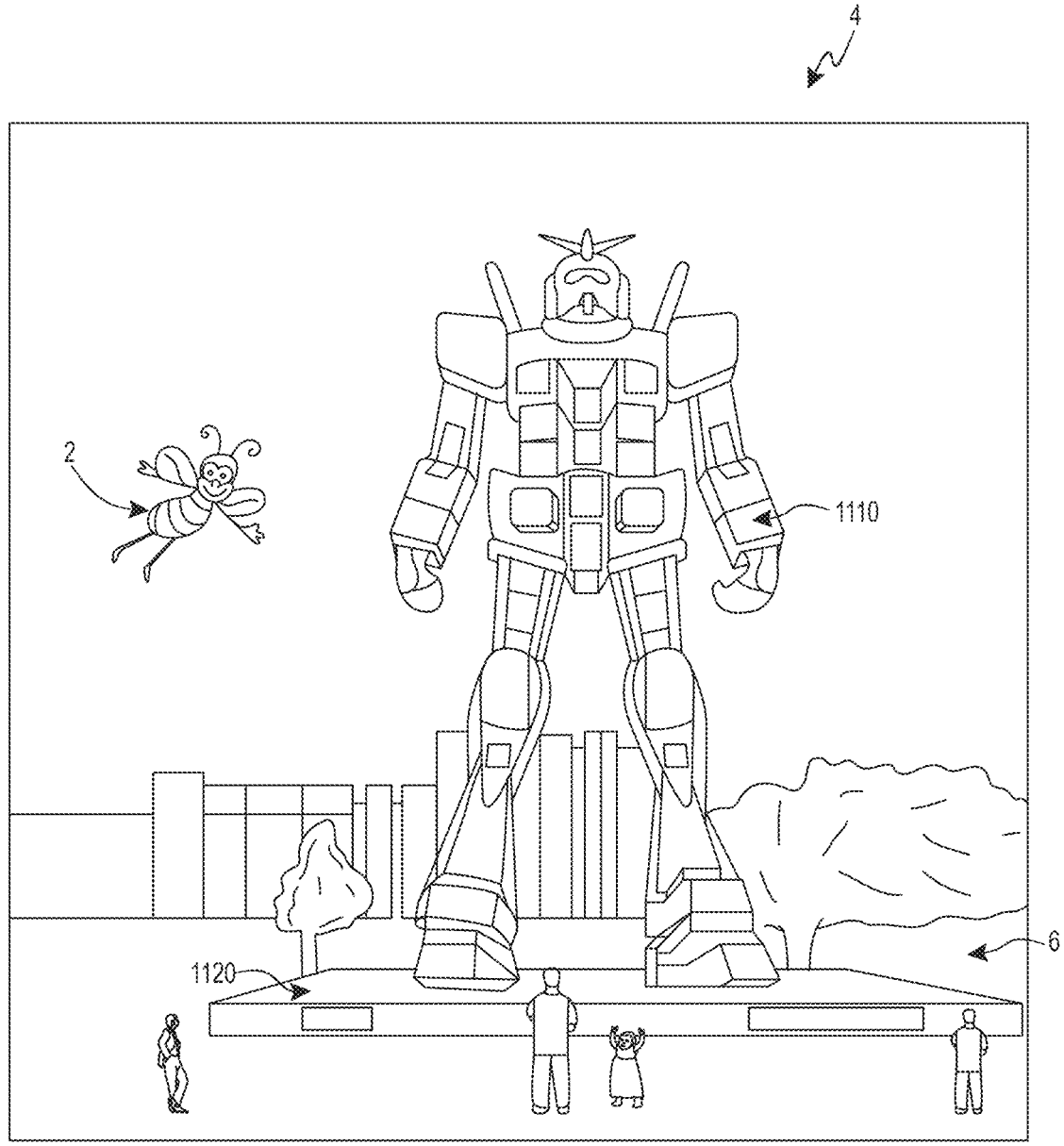
FIG. 1 illustrates certain aspects of an augmented reality system presentation to a user.

With a configuration as described above, wherein there is one world model that can reside on cloud computing resources and be distributed from there, such world can be "passable" to one or more users in a relatively low bandwidth form preferable to trying to pass around real-time video data or the like. In some embodiments, the augmented experience of the person standing near the statue (i.e., as shown in FIG. 1) may be informed by the cloud-based world model, a subset of which may be passed down to them and their local display device to complete the view. A person sitting at a remote display device, which may be as simple as a personal computer sitting on a desk, can efficiently download that same section of information from the cloud and have it rendered on their display. Indeed, one person actually present in the park near the statue may take a remotely-located friend for a walk in that park, with the friend joining through virtual and augmented reality. The system will need to know where the street is, where the trees are, where the statue is—but with that information on the cloud, the joining friend can download from the cloud aspects of the scenario, and then start walking along as an augmented reality local relative to the person who is actually in the park.

3-D points may be captured from the environment, and the pose (i.e., vector and/or origin position information relative to the world) of the cameras that capture those images or points may be determined, so that these points or images may be "tagged", or associated, with this pose information. Then points captured by a second camera may be utilized to determine the pose of the second camera. In other words, one can orient and/or localize a second camera based upon comparisons with tagged images from a first camera. Then this knowledge may be utilized to extract textures, make maps, and create a virtual copy of the real world (because then there are two cameras around that are registered).

So, at the base level, in some embodiments a person-worn system may be utilized to capture both 3-D points and the 2-D images that produced the points, and these points and images may be sent out to a cloud storage and processing resource. They may also be cached locally with embedded pose information (e.g., cache the tagged images); so, the cloud may have on the ready (e.g, in available cache) tagged 2-D images (e.g., tagged with a 3-D pose), along with 3-D points. If a user is observing something dynamic (e.g., a scene with moving objects or features), he/she may also send additional information up to the cloud pertinent to the motion (for example, if looking at another person's face, the user can take a texture map of the face and push that up at an optimized frequency even though the surrounding world is otherwise basically static). As noted above, more information on object recognizers and the passable world model may be found in U.S. patent application Ser. No. 14/205,126, entitled "System and method for augmented and virtual reality", which is incorporated by reference in its entirety herein, along with the following additional disclosures, which relate to augmented and virtual reality systems such as those developed by Magic Leap, Inc. of Fort Lauderdale, Fla.: U.S. patent application Ser. No. 14/641,376; U.S. patent application Ser. No. 14/555,585; U.S. patent application Ser. No. 14/212,961; U.S. patent application Ser. No. 14/690,401; U.S. patent application Ser. No. 13/663,466; U.S. patent application Ser. No. 13/684,489; and U.S. Patent Application Ser. No. 62/298,993, each of which is incorporated by reference herein in its entirety.

In some embodiments, the use of such passable world information may permit identification and labelling of objects by spectroscopy to then pass between users. For example, in a clinical setting, a first caregiver operating a device implementing features of the present disclosure may map and detect cancerous tissue on a patient and assign and apply a virtual label, much like a metatag, to the tissue. A second caregiver similarly wearing such a device may then look at the same cancerous tissue cell cluster and receive notice of the virtual label identifying such cells without needing to engage in one or more of emitting light, receiving light, matching an absorption trait to a tissue, and labeling the tissue independently.

GPS and other localization information may be utilized as inputs to such processing. It will be appreciated that highly accurate localization of the user's head, totems, hand gestures, haptic devices etc. can facilitate displaying appropriate virtual content to the user, or passable virtual or augmented content among users in a passable world.

Figure 5:
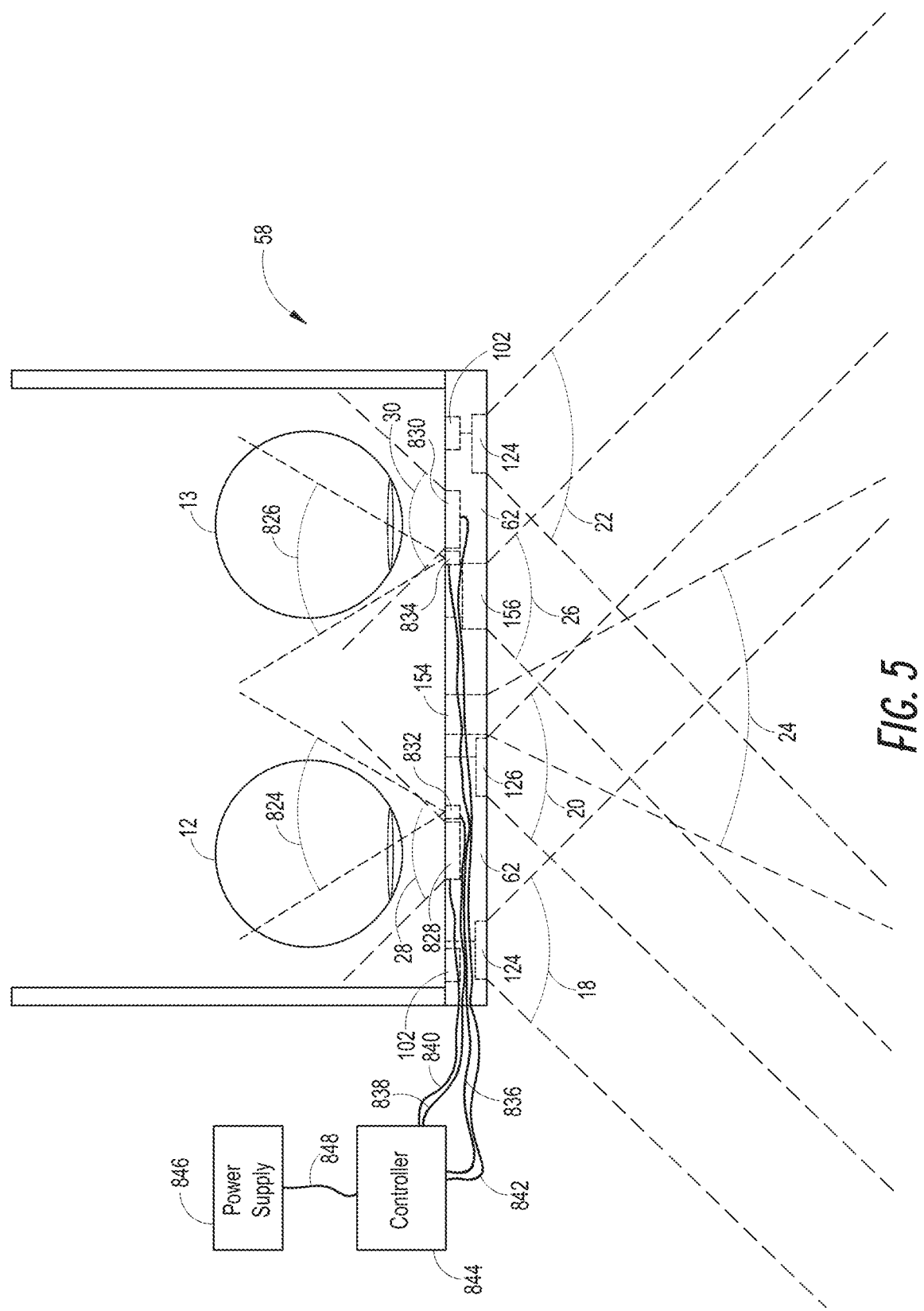
FIG. 5 illustrates a head-mounted spectroscopy system integrating AR/VR functionality according to some embodiments.

Referring to FIG. 5, a top orthogonal view of a head mountable component (58) of a wearable computing configuration is illustrated featuring various integrated components for an exemplary spectroscopy system. The configuration features two display elements (62—binocular—one for each eye), two forward-oriented cameras (124) for observing and detecting the world around the user, each camera (124) having an associated field of view (18, 22), and at least one spectroscopy array (126, described in greater detail in FIG. 6), with a field of view (20); also a forward-oriented relatively high resolution picture camera (156) with a field of view (26), one or more inertial measurement units (102), and a depth sensor (154) with an associated field of view (24), such as described in the aforementioned incorporated by reference disclosures. Facing toward the eyes (12, 13) of the user and coupled to the head mounted component (58) frame are eye tracking cameras (828, 830) and inward emitters and receivers (832, 834). One of skill in the art will appreciate the inward emitters and receivers (832, 834) emit and receive light directed towards the eyes in irradiation pattern (824, 826) much in the same way spectroscopy array (126) does for outward objects in its field of view (20). These components, or combinations less inclusive of all components are operatively coupled such as by wire lead, to a controller (844), which is operatively coupled (848) to a power supply (846), such as a battery.

In some embodiments, the display elements (62) include one or more waveguides (e.g., a waveguide stack) which are optically transmissive and allow the user to "see" the world by receiving light from the world. The waveguides also receive light containing display information and propagate and eject the light to the user's eyes (12, 13), to thereby display an image to the user. Preferably, light propagating out of the waveguide provides particular, defined levels of wavefront divergence corresponding to different depth planes (e.g., the light forming an image of an object at a particular distance from the user has a wavefront divergence that corresponds to or substantially matches the wavefront divergence of light that would reach the user from that object if real). For example, the waveguides may have optical power and may be configured to output light with selectively variable levels of wavefront divergence. It will be appreciated that this wavefront divergence provides cues to accommodation for the eyes (12, 13). In addition, the display elements (62) utilize binocular disparity to further provide depth cues, e.g. cues to vergence of the eyes (12, 13). Advantageously, the cues to accommodation and cues to vergence may match, e.g., such that they both correspond to an object at the same distance from the user. This accommodation-vergence matching facilitates the long-term wearability of a system utilizing the head-mounted member (58).

With continued reference to FIG. 5, preferably, each emitter (126, 832, 834) is configured to controllably emit electromagnetic radiation in two or more wavelengths, such as about 660 nm, and about 940 nm, such as by LEDs, and preferably the fields of irradiation (824, 826) are oriented to irradiate targeted objects or surfaces. In some embodiments, targeted objects are inward, such as eyes (12, 13) and irradiation patterns (824, 826) may be fixed or broadened/narrowed to target specific areas of an eye in response to an eye tracking camera data point. In some embodiments, targeted objects are outward (e.g., away from the user), and the irradiation pattern within the field of view (20) of spectroscope array (126) conforms to a gaze of the eyes (12, 13) determined from eye tracking cameras (828, 830).

In some embodiments, the gaze may be understood to be a vector extending from the user's eye, such as extending from the fovea through the lens of the eye, and the emitters (832, 834) may output infrared light on the user's eyes, and reflections from the eye (e.g., corneal reflections) may be monitored. A vector between a pupil center of an eye (e.g., the display system may determine a centroid of the pupil, for instance through infrared imaging) and the reflections from the eye may be used to determine the gaze of the eye. In some embodiments, when estimating the position of the eye, since the eye has a sclera and an eyeball, the geometry can be represented as two circles layered on top of each other. The eye pointing vector may be determined or calculated based on this information. Also the eye center of rotation may be estimated since the cross section of the eye is circular and the sclera swings through a particular angle. This may result in a vector distance because of autocorrelation of the received signal against known transmitted signal, not just ray traces. The output may be seen as a Purkinje image 1400 which may in turn be used to track movement of the eyes.

One of skill in the art will appreciate other ways to determine an irradiation pattern within field of view (20) such as by head pose information determined by one or more of IMU (102).

In some embodiments, the emitters may be configured to emit wavelengths simultaneously, or sequentially, with controlled pulsatile emission cycling. The one or more detectors (126, 828, 830) may comprise photodiodes, photodetectors, and/or digital camera sensors, and preferably are positioned and oriented to receive radiation that has encountered the targeted tissue or material or object otherwise. The one or more electromagnetic radiation detectors (126, 828, 830) may comprise a digital image sensor comprising a plurality of pixels, wherein the controller (844) is configured to automatically detect a subset of pixels which are receiving the light reflected after encountering a target object, and to use such subset of pixels to produce an output.

Figure 7A:
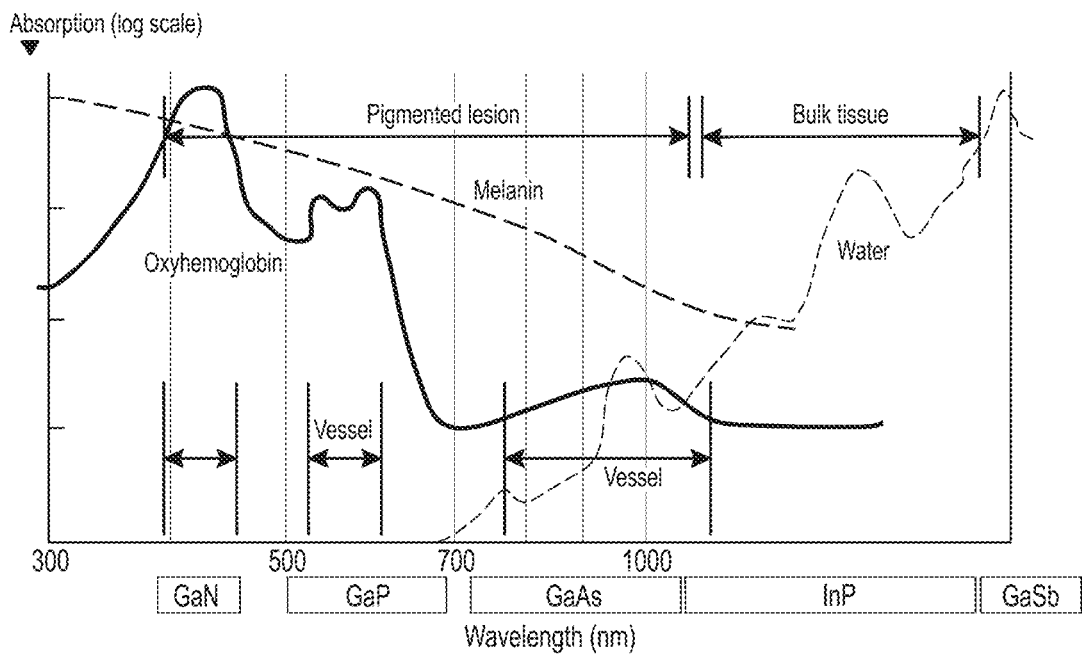
FIGS. 7A-7B are an example light saturation curve chart indicative of select properties by wavelengths.
Figure 7B:
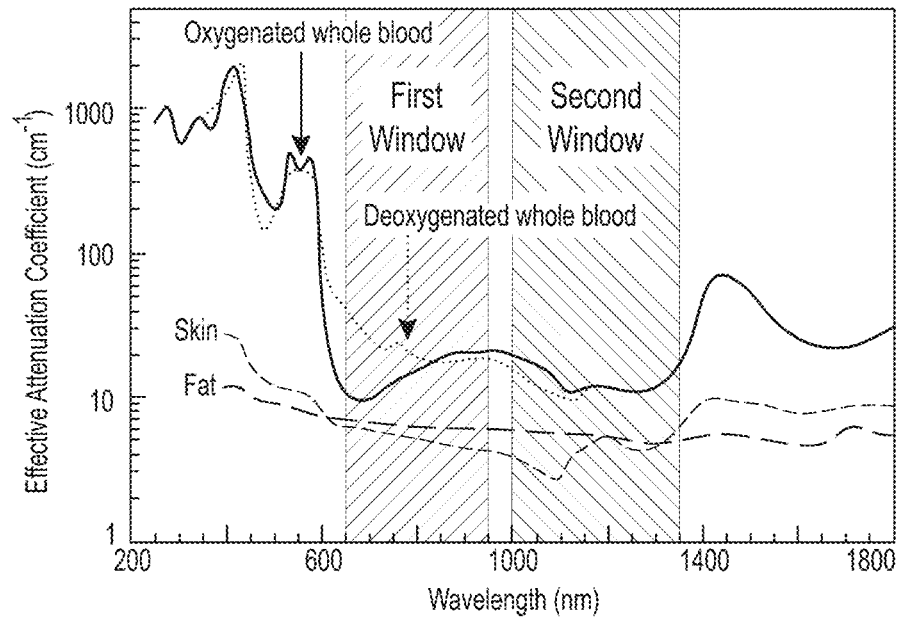

In some embodiments, the output is a function of matching received light against emitted light to a target from an absorption database of materials and material properties. For example, in some embodiments, an absorption database comprises a plurality of absorption charts such as depicted in FIGS. 7A and 7B. It will be appreciated that a database comprising charts may include electronic representations or transformations of the information in the charts, and the use of the term charts herein includes such representations or transformations. FIGS. 7A and 7B is merely used as an example, but demonstrates various tissue properties that may be detected from a given system emitting light from a particular light source and receiving light of a particular wavelength and/or light property to determine the probability of an observed target being a particular tissue or having particular properties within the tissue. Other charts, such as either saturation curves or calibration curves, may be selectively accessed by a user. For example, a user could choose absorption databases for a particular light source or wavelength patterns and then look around until the spectroscopy system identifies material matching the properties requested. Such an embodiment may be termed a "closed search," or one that looks for specific properties as opposed to an "open search" that looks at any target and then searches databases for matches on the light properties detected.

The controller (844) may be configured to automatically detect a subset of pixels within a field of view (124, or 126, or 824, 826, FIG. 5) based at least in part upon reflected light properties differences amongst signals associated with the pixels. For example, the controller (844) may be configured to automatically detect the subset of pixels based at least in part upon reflected light absorption differences amongst signals associated with the pixels. Without being limited by theory, light impacting upon an object will reflect, transmit (absorb), or scatter upon striking the object, such that R+T+S=1 (with R=reflection from the object, T=transmission/absorption into the object, and S=scatter from the object). If a particular subset of pixels reflects a higher proportion of light relative to surrounding subpixels, the controller may isolate these subpixels or note or register the pixel location for these different properties in a memory system. In some embodiments, the pixel location are stored in a passable world mapping system as dense or sparse mapping points such as additional users of a head mounted display system access the map, the subset of pixels are passed to the additional user and accessed and/or displayed on the second user's display.

Figure 6:
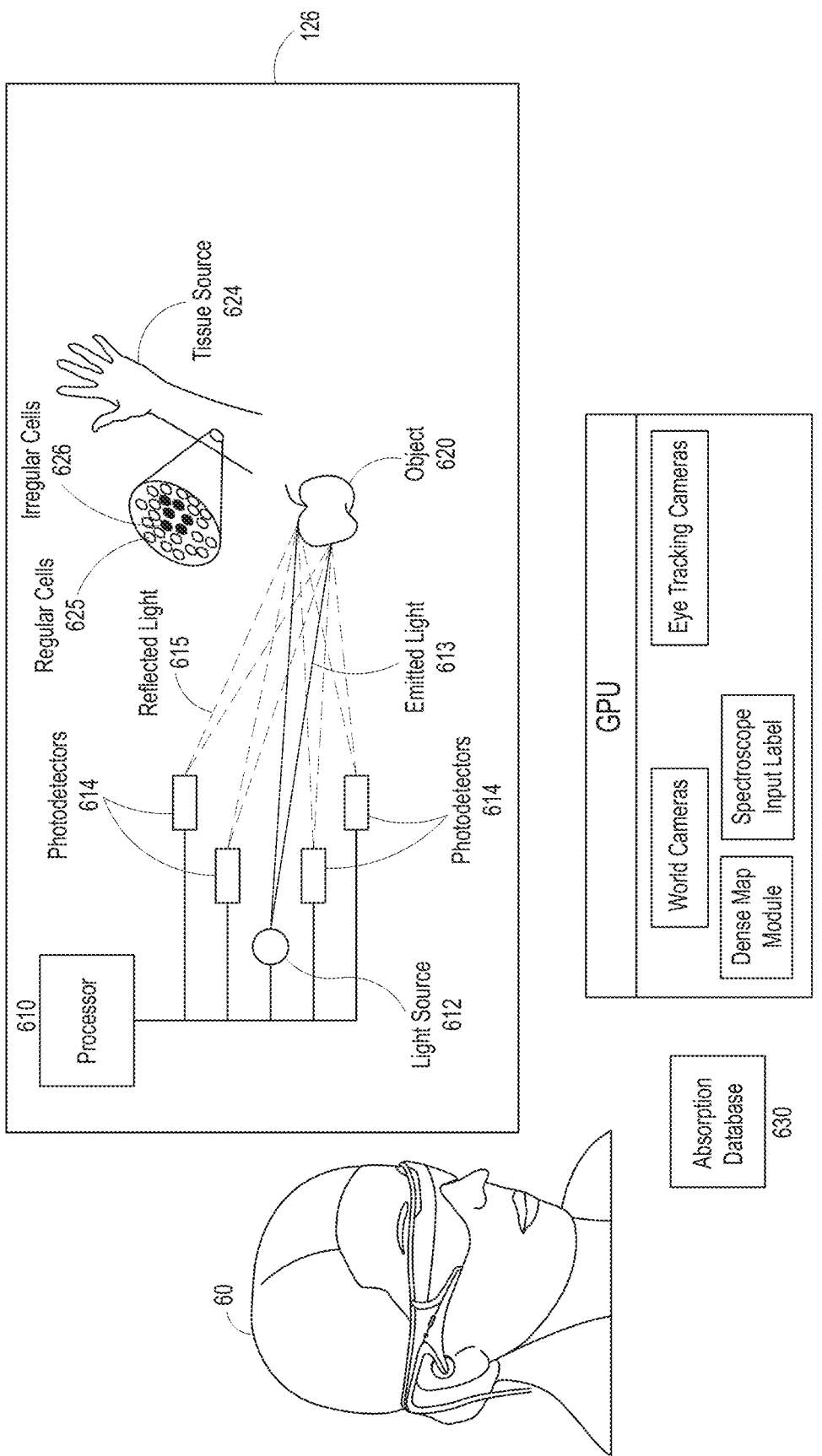
FIG. 6 illustrates various aspects of a wearable AR/VR system featuring integrated spectroscopy modules according to some embodiments.

Referring to FIG. 6, a spectroscopy array (126) may comprise a light source (612) emitting light (613) towards a target object (620). In some embodiments, the light source (612) is an electromagnetic emitter such as light emitting diodes. In some embodiments, the direction of emitted light (613) is substantially the same as a gaze orientation of a user (60) or a head pose orientation of a user (60). In some embodiments, photodetectors (614) capture reflected light (615) from the target object. In some embodiments, a processor (610), which may be controller (844) depicted in FIG. 5, determines an absorption property between emitted light (613) and reflected light (615) and matches the property from absorption database (630). In some embodiments, absorption database (630) is stored on a local processing module such as module (70) depicted in FIG. 2A for example; in some embodiments, absorption database (630) is stored on remote processing module (72) such as the one depicted in FIG. 2A.

Object (620) is depicted as an apple in FIG. 6 for simplicity, and though food properties have their respective light absorption properties and embodiments of the invention may be used to identify food by its light properties, more sophisticated uses are also envisioned. In some embodiments, outward facing spectroscopy array (126) identifies tissue source (624), e.g., an arm as depicted for illustrative purposes. Emitted light (613) may impact upon tissue source (624) and reflected light (615) may indicate the presence of irregular cells (626) amongst regular cells (625). As light source (612) irradiates tissue source (624), irregular cells (626) will return a different light property to photodetectors (614) than regular cells (625). Irregular cells (626) may be cancerous, be part of scar tissue, or even healthy cells amongst the tissue simply indicating or having a difference with surrounding cells, for example indicating where blood vessels or bone within tissue source (624) may be located. In some embodiments, regular cells constitute the majority of cells in a sample under analysis and irregular cells constitute a minority of the cells of the sample, the irregular cells exhibiting a different detectable property than the regular cells. In some embodiments, real world cameras capturing images on a pixel level may mark such irregular cells (626). As previously described, one such marking may be a labeling system applying a textual image proximate to the irregular cells (626), another such labeling system may be a color overlay onto irregular cells (626), as seen through the display element 62 (FIG. 5).

Thus, with reference again to FIG. 5, a system is presented for determining tissue properties or materials otherwise through a wearable computing system, such as one for AR or VR, comprising: a head-mounted member (58) removably coupleable to the user's head; one or more electromagnetic radiation emitters (126, 832, 834) coupled to the head-mounted member (58) and configured to emit light with at least two different wavelengths in inward directions or outwards directions, one or more electromagnetic radiation detectors (126, 828, 830) coupled to the head-mounted member and configured to receive light reflected after encountering a target object; and a controller (844) operatively coupled to the one or more electromagnetic radiation emitters (126, 832, 834) and one or more electromagnetic radiation detectors (126, 828, 830) and configured to cause the one or more electromagnetic radiation emitters to emit pulses of light while also causing the one or more electromagnetic radiation detectors to detect levels of light absorption related to the emitted pulses of light, and to produce a displayable output.

The head-mounted member (58) may comprise frame configured to fit on the user's head, e.g., an eyeglasses frame. The eyeglasses frame may be a binocular eyeglasses frame; alternative embodiments may be monocular. The one or more emitters (126, 832, 834) may comprise a light source, for example at least one light emitting diode or other electromagnetic radiation emitter, emitting light at multiple wavelengths. The plurality of light sources may be configured to preferably emit at two wavelengths of light, e.g., a first wavelength of about 660 nanometers, and a second wavelength of about 940 nanometers.

In some embodiments, the one or more emitters (126, 832, 834) may be configured to emit light at the respective wavelengths sequentially. In some embodiments, the one or more emitters (126, 832, 834) may be configured to emit light at the respective wavelengths simultaneously. The one or more electromagnetic radiation detectors (126, 828, 830) may comprise a device selected from the group consisting of: a photodiode, a photodetector, and a digital camera sensor. The controller (844) may be further configured to cause the plurality of light emitting diodes to emit a cyclic pattern of first wavelength on, then second wavelength on, then both wavelengths off, such that the one or more electromagnetic radiation detectors detect the first and second wavelengths separately. The controller (844) may be configured to cause the plurality of light emitting diodes to emit a cyclic pattern of first wavelength on, then second wavelength on, then both wavelengths off, in a cyclic pulsing pattern about thirty times per second. The controller (844) may be configured to calculate a ratio of first wavelength light measurement to second wavelength light measurement, and wherein this ratio is converted to an oxygen saturation reading via a lookup table based at least in part upon the Beer-Lambert law.

The controller (844) may be configured to operate the one or more emitters (126, 832, 834) and one or more electromagnetic radiation detectors (126, 828, 830) to function as a head-mounted spectroscope. The controller (844) may be operatively coupled to an optical element (62) coupled to the head-mounted member (58) and viewable by the user, such that the output of the controller (844) that is indicative of a particular material property or tissue property may be viewed by the user through the optical element (62).

FIG. 7A is an example light property absorption chart that may be referenced by an absorption database (630, FIG. 6). As depicted, various light source types, such as IR, NIR, or light emitting diodes in the visible spectrum may be optimal for detecting certain tissues and properties within the tissue. In some embodiments, an absorption ratio or scatter in calibration curve is computed from emitted light to reflected light and applied to the given absorption database (630) such as depicted in FIG. 7A to determine the underlying tissue and/or properties within or determine abnormalities.

FIG. 7B depicts potential "overlap" of wavelengths. As depicted, "oxygenated blood" may overlap with "deoxygenated blood" at certain wavelengths, muting the results that a spectroscopic processes may provide. To avoid this potential overlap, in some embodiments, light at a second different wavelength is emitted to provide a second source of light to measure and compare.

FIG. 8 illustrates a method (850) for using a wearable AR/VR system featuring spectroscopy components to identify tissue or properties within tissue. Method (850) begins at (851) with the system orienting light sources to a target object. In some embodiments, the orienting has light sources directed inwards towards the eyes of a user, and may be fixed or scanning the eye such as scanning the retina. In some embodiments, the orienting is by determining an eye gaze or head pose of the user and orienting a light source in substantially the same direction towards a target object within such gaze or pose field of view, or towards feature landmarks or target objects.

In some embodiments, at (852) light sources emit light in an irradiation pattern towards the target object or surface. In some embodiments, the light is pulsed at timed intervals by a timer. In some embodiments, the light source emits light of at least one wavelength and at (854) radiation detectors, such as photo detectors, receive reflected light. In some embodiments, the detectors are also operatively coupled to a timer to indicate if received light was initially pulsed at a certain time to determine changes in light properties upon reflecting on the target object. In some embodiments, (852) begins concurrent with mapping at (853) but this sequence is not necessarily so.

In some embodiments, real world capturing systems may begin to map the target object at (853). In some embodiments, such mapping may include receiving passable world data of the target object. In some embodiments, mapping may include depth sensor analysis of the contours of the target object. In some embodiments, mapping may include building a mesh model of the items within the field of view and referencing them for potential labeling. In some embodiments, the target object is not a specific object within the field of view that may be captured by a depth sensor, but rather is a depth plane within the field of view itself.

In some embodiments, at (855) a controller analyzes the emitted light compared to the received light, such as under the Beer-Lambert law or the optical density relationship (described below) or scatter pattern of a calibration curve. In some embodiments, at (856) the compared light properties are referenced in an absorption database, either locally stored on the system or remotely accessed through the system, to identify the tissue or tissue property of the target object. In some embodiments, an absorption database may comprise saturation light charts, such as the one depicted in FIG. 4B, or may comprise calibration curves of particular light wavelengths.

In some embodiments, at (854) the radiation detectors do not receive light of different wavelengths than the wavelength of the light emitted at (852), and a controller cannot conduct a spectroscopic analysis. Such an occasion would occur as in FIG. 7B, with overlap of wavelengths in certain ranges for oxygenated and deoxygenated blood. In some embodiments, at (854*a*) no wavelength difference is detected between the emitted light and received light, and substep (854*b*) initiates by emitting light at another different wavelength than that emitted at (852). The new light emitted and light received information is then delivered to a controller at (855).

In some embodiments, real world cameras may additionally, subsequent to mapping a target object (853) and potentially concurrent with each of (852 through 856), identify subpixels within a field of field indicative of irregularities at (857). For example, in some embodiments, color contrast between pixels is detected during real world capture at (853) and at (857) these pixels are further altered to highlight such contrast as potential unhealthy cells. In some embodiments, real world capture (853) detects irregular lines among pixel clusters and at (857) the pixels bounded by the irregular lines are marked (such as by a virtual color overlay) on a user display.

In some embodiments, method (850) terminates at (858) with the system displaying the tissue or material property of the tissue to the user. In some embodiments, display may comprise a textual label virtually displayed proximate to the target object, an audio label describing the target object as determined from the absorption database (630), or a virtual image of similar tissue or object identified by absorption database (630) juxtaposed proximate to the target object.

In some embodiments, a significant amount of the spectroscopy activity is implemented with software operated by the controller (844), such that an initial task of locating desired targets (e.g., blood vessels, muscle tissue, bone tissue, or other tissue and at a desired depth) is conducted using digital image processing (such as by color, grayscale, and/or intensity thresholding analysis using various filters. Such targeting may be conducted using pattern, shape recognition or texture recognition. Cancerous cells or otherwise irregular cells commonly have irregular borders. A camera system may identify a series of pixels within a camera field of view (such as cameras 124 and field of view 18, 22 of FIG. 5) with an irregular, non-linear pattern and prompt attention to identify such as a border to a potentially unhealthy cell. Alternatively, the software and controller may be configured to use the intensity of the center of the targeted object and the intensity of the surrounding objects/tissue to determine contrast/optical density with the targeted object to determine abnormalities. Such measures may merely be used to identify areas of interest for spectroscopic scan consistent with this disclosure, and not necessarily a means of identifying tissue itself. Further, as previously described with reference to irregular cells (626) in FIG. 6, an augmented reality system may overlay a label or color pattern within the borders of the potentially unhealthy cells to flag them/highlight them against surrounding healthy cells.

In some embodiments, the controller (844) may be utilized to calculate density ratios (contrast) and to calculate the oxygen saturation from the density ratios of various pulse oximetry properties in blood vessels. Vessel optical density ("O.D.") at each of the two or more emitted wavelengths may be calculated using the formula:

$$ODvessel = -\log_{10}(Iv/It)$$

wherein ODvessel is the optical density of the vessel; Iv is the vessel intensity; and It is the surrounding tissue intensity.

Oxygen saturation (also termed "SO2") in a blood vessel may be calculated as a linear ratio of vessel optical densities (OD ratio, or "ODR") at the two wavelengths, such that:

$$SO_2 = ODR = OD_{firstwavelength}/OD_{secondwavelength}$$

In one embodiment, wavelengths of about 570 nm (sensitive to deoxygenated hemoglobin) and about 600 nm (sensitive to oxygenated hemoglobin) may be utilized in vessel oximetry, such that $SO2 = ODR = OD_{600nm}/OD570$ nm; such formula does not account for adjusting the ratio by a calibration coefficient.

The above formulas are merely examples of references for calculating material properties. One of skill in the art will appreciate many other tissue properties and relationships a controller may determine.

It will be appreciated that utilizing the controller (844) to perform calculations and/or make determinations may involve performing calculations locally on a processor within the controller (844). In some other embodiments, performing calculations and/or making determinations with the controller (844) may involve utilizing the controller to interface with external computing resources, e.g., resources in the cloud (46) such as servers (110).

Computer Vision

As discussed above, the spectroscopy system may be configured to detect objects in or features (e.g. properties) of objects in the environment surrounding the user. In some embodiments, objects or properties of objects present in the environment may be detected using computer vision techniques. For example, as disclosed herein, the spectroscopy system's forward-facing camera may be configured to image an object and the system may be configured to perform image analysis on the images to determine the presence of features on the objects. The system may analyze the images, absorption determinations, and/or reflected and/or scattered light measurements acquired by the outward-facing imaging system to object recognition, object pose estimation, learning, indexing, motion estimation, or image restoration, etc. One or more computer vision algorithms may be selected as appropriate and used to perform these tasks. Non-limiting examples of computer vision algorithms include: Scale-invariant feature transform (SIFT), speeded up robust features (SURF), oriented FAST and rotated BRIEF (ORB), binary robust invariant scalable keypoints (BRISK), fast retina keypoint (FREAK), Viola-Jones algorithm, Eigenfaces approach, Lucas-Kanade algorithm, Horn-Schunk algorithm, Mean-shift algorithm, visual simultaneous location and mapping (vSLAM) techniques, a sequential Bayesian estimator (e.g., Kalman filter, extended Kalman filter, etc.), bundle adjustment, Adaptive thresholding (and other thresholding techniques), Iterative Closest Point (ICP), Semi Global Matching (SGM), Semi Global Block Matching (SGBM), Feature Point Histograms, various machine learning algorithms (such as e.g., support vector machine, k-nearest neighbors algorithm, Naive Bayes, neural network (including convolutional or deep neural networks), or other supervised/unsupervised models, etc.), and so forth.

As discussed herein, the objects or features (including properties) of objects may be detected based on one or more criteria (e.g., absorbance, light reflection, and/or light scattering at one or more wavelengths). When the spectroscopy system detects the presence or absence of the criteria in the ambient environment using a computer vision algorithm or using data received from one or more sensor assemblies (which may or may not be part of the spectroscopy system), the spectroscopy system may then signal the presence of the object or feature.

One or more of these computer vision techniques may also be used together with data acquired from other environmental sensors (such as, e.g., microphone, GPS sensor) to detect and determine various properties of the objects detected by the sensors.

Machine Learning

A variety of machine learning algorithms may be used to learn to identify the presence of objects or features of objects. Once trained, the machine learning algorithms may be stored by the spectroscopy system. Some examples of machine learning algorithms may include supervised or non-supervised machine learning algorithms, including regression algorithms (such as, for example, Ordinary Least Squares Regression), instance-based algorithms (such as, for example, Learning Vector Quantization), decision tree algorithms (such as, for example, classification and regression trees), Bayesian algorithms (such as, for example, Naive Bayes), clustering algorithms (such as, for example, k-means clustering), association rule learning algorithms (such as, for example, a-priori algorithms), artificial neural network algorithms (such as, for example, Perceptron), deep learning algorithms (such as, for example, Deep Boltzmann Machine, or deep neural network), dimensionality reduction algorithms (such as, for example, Principal Component Analysis), ensemble algorithms (such as, for example, Stacked Generalization), and/or other machine learning algorithms. In some embodiments, individual models may be customized for individual data sets. For example, the wearable device may generate or store a base model. The base model may be used as a starting point to generate additional models specific to a data type (e.g., a particular user), a data set (e.g., a set of absorbance, light reflection, and/or light scattering values obtained at one or more wavelengths), conditional situations, or other variations. In some embodiments, the spectroscopy system may be configured to utilize a plurality of techniques to generate models for analysis of the aggregated data. Other techniques may include using pre-defined thresholds or data values.

The criteria for detecting an object or feature of an object may include one or more threshold conditions. If the analysis of the data acquired by a sensor (e.g., a camera or photodetector) indicates that a threshold condition is passed, the spectroscopy system may provide a signal indicating the detection the presence of the object in the ambient environment. The threshold condition may involve a quantitative and/or qualitative measure. For example, the threshold condition may include a score or a percentage associated with the likelihood of the object and/or feature being present. The spectroscopy system may compare the score calculated from the sensor's data with the threshold score. If the score is higher than the threshold level, the spectroscopy system may signal detection of the presence of an object or object feature. In some other embodiments, the spectroscopy system may signal the absence of the object or feature if the score is lower than the threshold.

It will be appreciated that each of the processes, methods, and algorithms described herein and/or depicted in the figures may be embodied in, and fully or partially automated by, code modules executed by one or more physical computing systems, hardware computer processors, application-specific circuitry, and/or electronic hardware configured to execute specific and particular computer instructions. A code module may be compiled and linked into an executable program, installed in a dynamic link library, or may be written in an interpreted programming language. In some embodiments, particular operations and methods may be performed by circuitry that is specific to a given function. In some embodiments, the code modules may be executed by hardware in the controller (844) (FIG. 5) and/or in the cloud (46) (e.g., servers (110)).

Further, certain embodiments of the functionality of the present disclosure are sufficiently mathematically, computationally, or technically complex that application-specific hardware or one or more physical computing devices (utilizing appropriate specialized executable instructions) may be necessary to perform the functionality, for example, due to the volume or complexity of the calculations involved or to provide results substantially in real-time. For example, a video may include many frames, with each frame having millions of pixels, and specifically programmed computer hardware is necessary to process the video data to provide a desired image processing task or application in a commercially reasonable amount of time.

Code modules or any type of data may be stored on any type of non-transitory computer-readable medium, such as physical computer storage including hard drives, solid state memory, random access memory (RAM), read only memory (ROM), optical disc, volatile or non-volatile storage, combinations of the same and/or the like. In some embodiments, the non-transitory computer-readable medium may be part of one or more of the local processing and data module (70, FIG. 2C), the remote processing module (72, FIG. 2D), and remote data repository (74, FIG. 2D). The methods and modules (or data) may also be transmitted as generated data signals (e.g., as part of a carrier wave or other analog or digital propagated signal) on a variety of computer-readable transmission mediums, including wireless-based and wired/cable-based mediums, and may take a variety of forms (e.g., as part of a single or multiplexed analog signal, or as multiple discrete digital packets or frames). The results of the disclosed processes or process steps may be stored, persistently or otherwise, in any type of non-transitory, tangible computer storage or may be communicated via a computer-readable transmission medium.

Any processes, blocks, states, steps, or functionalities in flow diagrams described herein and/or depicted in the attached figures should be understood as potentially representing code modules, segments, or portions of code which include one or more executable instructions for implementing specific functions (e.g., logical or arithmetical) or steps in the process. The various processes, blocks, states, steps, or functionalities may be combined, rearranged, added to, deleted from, modified, or otherwise changed from the illustrative examples provided herein. In some embodiments, additional or different computing systems or code modules may perform some or all of the functionalities described herein. The methods and processes described herein are also not limited to any particular sequence, and the blocks, steps, or states relating thereto may be performed in other sequences that are appropriate, for example, in serial, in parallel, or in some other manner. Tasks or events may be added to or removed from the disclosed example embodiments. Moreover, the separation of various system components in the embodiments described herein is for illustrative purposes and should not be understood as requiring such separation in all embodiments. It should be understood that the described program components, methods, and systems may generally be integrated together in a single computer product or packaged into multiple computer products.

Various exemplary embodiments of the invention are described herein. Reference is made to these examples in a non-limiting sense. They are provided to illustrate more broadly applicable aspects of the invention. Various changes may be made to the invention described and equivalents may be substituted without departing from the true spirit and scope of the invention. In addition, many modifications may be made to adapt a particular situation, material, composition of matter, process, process act(s) or step(s) to the objective(s), spirit or scope of the present invention. Further, as will be appreciated by those with skill in the art that each of the individual variations described and illustrated herein has discrete components and features which may be readily separated from or combined with the features of any of the other several embodiments without departing from the scope or spirit of the present inventions. All such modifications are intended to be within the scope of claims associated with this disclosure.

The invention includes methods that may be performed using the subject devices. The methods may comprise the act of providing such a suitable device. Such provision may be performed by the end user. In other words, the "providing" act merely requires the end user obtain, access, approach, position, set-up, activate, power-up or otherwise act to provide the requisite device in the subject method. Methods recited herein may be carried out in any order of the recited events which is logically possible, as well as in the recited order of events.

Exemplary aspects of the invention, together with details regarding material selection and manufacture have been set forth above. As for other details of the present invention, these may be appreciated in connection with the above-referenced patents and publications as well as generally known or appreciated by those with skill in the art. The same may hold true with respect to method-based aspects of the invention in terms of additional acts as commonly or logically employed.

In addition, though the invention has been described in reference to several examples optionally incorporating various features, the invention is not to be limited to that which is described or indicated as contemplated with respect to each variation of the invention. Various changes may be made to the invention described and equivalents (whether recited herein or not included for the sake of some brevity) may be substituted without departing from the true spirit and scope of the invention. In addition, where a range of values is provided, it is understood that every intervening value, between the upper and lower limit of that range and any other stated or intervening value in that stated range, is encompassed within the invention.

Also, it is contemplated that any optional feature of the inventive variations described may be set forth and claimed independently, or in combination with any one or more of the features described herein. Reference to a singular item, includes the possibility that there are plural of the same items present. More specifically, as used herein and in claims associated hereto, the singular forms "a," "an," "said," and "the" include plural referents unless specifically stated otherwise. In other words, use of the articles allow for "at least one" of the subject item in the description above as well as claims associated with this disclosure. It is further noted that such claims may be drafted to exclude any optional element. As such, this statement is intended to serve as antecedent basis for use of such exclusive terminology as "solely," "only" and the like in connection with the recitation of claim elements, or use of a "negative" limitation.

Without the use of such exclusive terminology, the term "comprising" in claims associated with this disclosure shall allow for the inclusion of any additional element—irrespective of whether a given number of elements are enumerated in such claims, or the addition of a feature could be regarded as transforming the nature of an element set forth in such claims. Except as specifically defined herein, all technical and scientific terms used herein are to be given as broad a commonly understood meaning as possible while maintaining claim validity.

The breadth of the present invention is not to be limited to the examples provided and/or the subject specification, but rather only by the scope of claim language associated with this disclosure.

What is claimed is:

1. A wearable spectroscopy system comprising:
   a frame removably coupleable to a user's head;
   a head-mountable display attached to the frame;
   at least one outward-facing light source coupled to the frame and configured to emit light with at least two different wavelengths;
   at least one electromagnetic radiation detector coupled to the frame and configured to receive reflected light from a target object irradiated by the emitted light;
   an absorption database of light absorption properties of at least one material;
   a controller operatively coupled to the at least one outward-facing light source and the at least one electromagnetic radiation detector, the controller configured to cause:
      emission of pulses of light by the at least one outward-facing light source;
      detection, by the at least one electromagnetic radiation detector, of levels of light absorption related to the emitted pulses of light and reflected light from the target object; and
      matching of detected levels of light absorption with light absorption properties stored in the absorption database; and
   a graphics processor unit configured to display an output to the user.

2. The system of claim 1, wherein the at least one outward-facing light source comprises a plurality of light emitting diodes.

3. The system of claim 1, wherein the at least one outward-facing light source is configured to emit electromagnetic radiation at a first wavelength of about 660 nanometers, and a second wavelength of about 940 nanometers.

4. The system of claim 1, wherein the at least one outward-facing light source is configured to emit electromagnetic radiation at the two predetermined wavelengths sequentially.

5. The system of claim 1, wherein the at least one outward-facing light source is configured to emit electromagnetic radiation at the two predetermined wavelengths simultaneously.

6. The system of claim 1, wherein the controller is further configured to cause the at least one outward-facing light source to emit a cyclic pattern of a first wavelength on, then a second wavelength on, then both first and second wavelengths off, such that the at least one electromagnetic radiation detector detects the first and second wavelengths separately.

7. The system of claim 1, wherein the controller is configured to calculate a ratio of first wavelength light measurement to second wavelength light measurement, and wherein the system is configured to convert the ratio to a tissue property based on the absorption database.

8. The system of claim 7, wherein the controller is operatively coupled to an optical element coupled to the head-mountable display and viewable by the user, wherein the system is configured to provide the output based on the tissue property, wherein the output is viewable by the user through the optical element.

9. The system of claim 7, wherein the tissue property comprises at least one property selected from the group consisting of: a tissue type, an estimated blood saturation level, a presence of abnormal cells, a presence of cancerous cells.

10. The system of claim 1, wherein the at least one electromagnetic radiation detector comprises a device selected from the group consisting of a photodiode and a photodetector.

11. The system of claim 1, wherein the at least one electromagnetic radiation detector comprises a digital image sensor.

12. The system of claim 11, wherein the digital image sensor comprises a plurality of pixels, and wherein the controller is configured to automatically detect a subset of pixels which are receiving the light reflected after encountering a predetermined tissue property and to produce an output that displays the location of the subset of pixels indicating the predetermined tissue property.

13. The system of claim 1, wherein the head-mountable display further comprises an inertial measurement unit positional system.

14. The system of claim 13, wherein the inertial measurement unit positional system determines a pose orientation of the user's head.

15. The system of claim 14, wherein the at least one outward-facing light source is configured to emit the light in a direction corresponding to the pose orientation of the user's head.

16. The system of claim 1, wherein the head-mountable display comprises a stack of waveguides configured to output light to an eye of the user.

\* \* \* \* \*